(12) United States Patent
Hu et al.

(10) Patent No.: US 7,153,827 B1
(45) Date of Patent: Dec. 26, 2006

(54) VASCULAR ENDOTHELIAL GROWTH FACTOR 2 AND METHODS OF USE

(75) Inventors: Jing-Shan Hu, Sunnyvale, CA (US); Craig A. Rosen, Laytonsville, MD (US); Liang Cao, South Horizons (HK)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/219,442

(22) Filed: Dec. 23, 1998

Related U.S. Application Data

(60) Division of application No. 08/999,811, filed on Dec. 24, 1997, now Pat. No. 5,932,540, which is a continuation-in-part of application No. 08/465,968, filed on Jun. 6, 1995, now Pat. No. 6,608,182, and a continuation-in-part of application No. 08/207,550, filed on Mar. 8, 1994, now abandoned.

(51) Int. Cl.
*A61K 38/00* (2006.01)
*A01N 37/18* (2006.01)
*C07K 1/00* (2006.01)
*C07K 14/00* (2006.01)
*C07K 17/00* (2006.01)

(52) U.S. Cl. .......................... 514/12; 514/2; 530/350; 530/399

(58) Field of Classification Search ................ 530/399, 530/350; 514/2.12
See application file for complete search history.

(56) References Cited

U.S. PATENT DOCUMENTS

| | | | |
|---|---|---|---|
| 5,073,492 A | 12/1991 | Chen et al. ............ 435/240.2 |
| 5,194,596 A | 3/1993 | Tischer et al. | |
| 5,219,739 A | 6/1993 | Tischer et al. ............ 435/69.4 |
| 5,234,908 A | 8/1993 | Szabo et al. | |
| 5,240,848 A | 8/1993 | Keck et al. | |
| 5,283,354 A | 2/1994 | Lemischka | |
| 5,326,695 A | 7/1994 | Andersson et al. ........ 435/70.1 |
| 5,607,918 A | 3/1997 | Eriksson et al. | |
| 5,633,147 A | 5/1997 | Meissner et al. | |
| 5,652,225 A | 7/1997 | Isner | |
| 5,661,133 A | 8/1997 | Leiden et al. | |
| 5,693,622 A | 12/1997 | Wolff et al. | |
| 5,776,755 A | 7/1998 | Alitalo et al. | |
| 5,792,453 A | 8/1998 | Hammond et al. | |
| 5,840,693 A | 11/1998 | Eriksson et al. | |
| 5,861,301 A | 1/1999 | Terman et al. | |
| 5,932,540 A | 8/1999 | Hu et al. | |
| 5,935,820 A | 8/1999 | Hu et al. | |
| 6,040,157 A | 3/2000 | Hu et al. | |
| 6,121,246 A | 9/2000 | Isner | |
| 6,130,071 A | 10/2000 | Alitalo et al. | |
| 6,221,839 B1 | 4/2001 | Alitalo et al. | |
| 6,245,530 B1 | 6/2001 | Alitalo et al. | |
| 6,361,946 B1 | 3/2002 | Alitalo et al. | |
| 6,403,088 B1 | 6/2002 | Alitalo et al. | |
| 6,451,764 B1 | 9/2002 | Lee et al. | |
| 6,645,933 B1 | 11/2003 | Alitalo et al. | |
| 6,734,285 B1 | 5/2004 | Hu et al. | |
| 2002/0120123 A1 | 8/2002 | Rosen et al. | |
| 2004/0143103 A1 | 7/2004 | Hu et al. | |
| 2006/0014252 A1 | 1/2006 | Lyman | |

FOREIGN PATENT DOCUMENTS

| | | |
|---|---|---|
| AU | 710696 | 9/1999 |
| AU | B-70128/96 A1 | 9/1999 |
| EP | 0 186 084 A2 | 7/1986 |
| EP | 0 399 816 A1 | 11/1990 |
| EP | 0476983 | 3/1992 |
| EP | 0476983 A1 | 3/1992 |
| EP | 0 506 477 A1 | 6/1992 |
| EP | 0506477 | 9/1992 |
| JP | 64-38100 A | 2/1989 |
| JP | 2-117698 A | 5/1990 |
| WO | WO 91/02058 | 2/1991 |
| WO | WO 921/4748 | 9/1992 |
| WO | WO 94/11506 A1 | 5/1994 |
| WO | WO 95/19985 | 7/1995 |
| WO | WO 95/24414 | 9/1995 |
| WO | WO-95/24473 | 9/1995 |
| WO | WO 96/05856 | 2/1996 |
| WO | WO 96/39515 | 12/1996 |
| WO | WO-97/00271 | 1/1997 |
| WO | 9705250 | 2/1997 |
| WO | WO 97/05250 | 2/1997 |
| WO | 9709427 | 3/1997 |
| WO | WO-97/08320 | 3/1997 |
| WO | WO 97/09427 | 3/1997 |

(Continued)

OTHER PUBLICATIONS

Paulsson G. et al. Accession No. S08167. J. Molecular Biol. 211:331-349, 1990.*

(Continued)

*Primary Examiner*—Robert S. Landsman
(74) *Attorney, Agent, or Firm*—Sterne, Kessler, Goldstein & Fox, P.L.L.C.

(57) ABSTRACT

Disclosed are human VEGF2 polypeptides, biologically active, diagnostically or therapeutically useful fragments, analogs, or derivatives thereof, and DNA(RNA) encoding such VEGF2 polypeptides. Also provided are procedures for producing such polypeptides by recombinant techniques and antibodies and antagonists against such polypeptides. Such polypeptides may be used therapeutically for stimulating wound healing and for vascular tissue repair. Also provided are methods of using the antibodies and antagonists to inhibit tumor angiogenesis and thus tumor growth, inflammation, diabetic retinopathy, rheumatoid arthritis, and psoriasis.

240 Claims, 20 Drawing Sheets

FOREIGN PATENT DOCUMENTS

| | | |
|---|---|---|
| WO | 9717442 | 5/1997 |
| WO | WO 97/17442 | 5/1997 |
| WO | WO-97/19694 | 6/1997 |
| WO | WO 98/06844 | 2/1998 |
| WO | WO 98/07832 | 2/1998 |
| WO | WO 98/24811 | 6/1998 |
| WO | WO 98/33917 | 6/1998 |
| WO | WO 98/39035 | 9/1998 |
| WO | WO 98/49300 | 11/1998 |
| WO | WO 98/55619 | 12/1998 |
| WO | WO 98/56936 | 12/1998 |
| WO | WO 99/02545 | 1/1999 |
| WO | WO 99/08522 | 2/1999 |
| WO | WO 99/20749 | 4/1999 |
| WO | WO 99/21590 | 5/1999 |
| WO | 99/46364 | 9/1999 |
| WO | WO 99/46364 A1 | 9/1999 |
| WO | WO 00/45835 | 8/2000 |
| WO | WO 00/73430 A3 | 12/2000 |
| WO | WO 00/75163 A1 | 12/2000 |
| WO | WO 01/57226 A1 | 8/2001 |
| WO | WO 01/58956 A3 | 8/2001 |
| WO | WO 02/11769 A1 | 2/2002 |
| WO | WO 02/083704 A1 | 10/2002 |
| WO | WO 02/083849 A2 | 10/2002 |
| WO | WO 02/083850 A2 | 10/2002 |
| WO | WO 03/097660 A1 | 11/2003 |
| ZA | 9-403464 | 1/1996 |

OTHER PUBLICATIONS

Eichmann, A., et al., Development 125(4):743-752 (1998).
Pajusola, K., et al., Cancer Research. 52:5738-5743 (1992).
Pajusola, K., et al., Oncogene 8:2931-2937 (1993).
Tischer, et al., Biochemical and Biophysical Research Communications 165(3):1198-1206 (1989).
Leung, D.W., et al., Science 246:1306-1309 (1989).
Breier, G., et al., Development 114:521-532 (1992).
Ferrara, et al., Journal of Cellular Biochemistry 47:211-218 (1991).
George et al., Macromolecular Seq. and Syn. Selected Meth—Application, pp. 127-149 (1988).
U.S. Appl. No. 08/340,011, filed Nov. 1994.
U.S. Appl. No. 08/510,133, filed Aug. 1995.
U.S. Appl. No. 08/585,895, filed Jan. 1996.
U.S. Appl. No. 08/601,132, filed Feb. 1996.
U.S. Appl. No. 08/671,573, filed Jun. 1996.
U.S. Appl. No. 08/554,374, filed Nov. 1995.
U.S. Appl. No. 60/03491, filed Sep. 1995.
Betsholtz et al., Nature 320:695-699 (1986).
Claffey et al., J. Biol. Chem. 267(23):16317-16322 (1992).
Corson et al., Genomics 17:476-484 (1993).
Dignam et al., Gene 88:133-140 (1990).
Ferrara et al., Endocrine Rev. 13(1):18-32 (1992).
Finnerty et al., Oncogene, 8(11): 2293-2298 (1993).
Heldin et al. Growth Factors 8:245-252 (1993).
Hu et al., FASEB J., 11:498-504 (1997).
Joukov et al., EMBO J. 15(2):290-298 (1996).
Joukov et al., EMBO J. 16(13):3898-3911 (1997).
Kaipainen et al., J. Exp. Med. 178:2077-2088 (1993).
Keck et al., Science 246: 1309 (1989).
Kingsley, D., Genes & Development 8:133-146 (1994).
Kukk et al., Development, 122: 3829-37 (1996).
Lee et al, Proc. Natl. Acad. Sci. (USA), 93:1988-1992 (1996).
Maglione et al., Oncogene 8:925-931 (1993).
Maglione et al., Proc. Natl. Acad. Sci. (USA), 88:9267-9271 (1991).
Massague, J. Annu. Rev. Cell Biol. 6:597-641 (1990).
Matthews et al., Proc. Natl. Acad. Sci. (USA), 88:9026-9030 (1991).
Millauer et al., Cell 72:835-846 (1993).
Millauer et al., Nature 367:576-579 (1994).
Oltvai et al., Cell, 74:609-619 (1993).
Paulsson et al., J. Mol. Biol. 211:331-349 (1990).
Tanaka et al., Mol. Cell Biol. 7(5):1978-1983 (1987).
Terman et al., Oncogene 6:1677-1683 (1991).
Terman et al., Biochem. Biophys. Res. Commun. 187(3):1579-1586 (1992).
Tischer et. al., J. Biol.Chem. 266(18):11947-11954 (1991).
Tsujimoto et al., Proc. Natl. Acad. Sci (USA), 83:5214-5218 (1986).
GenBank Accession No. X68203 (1993).
GenBank Accession No. M95200 (1992).
GenBank Accession No. M24160 (1989).
GenBank Accession No. M24276 (1989).
GenBank Accession No. M24277 (1989).
GenBank Accession No. D88689 (1993).
GenBank Accession No. L07296 (1993).
GenBank Accession No. X54936 (1991).
GenBank Accession No. S57152 (1993).
GenBank Accession No. X59397 (1991).
GenBank Accession No. X52263 (1992).
GenBank Accession No. M63971 (1991).
GenBank Accession No. M63972 (1991).
GenBank Accession No. M63973 (1991).
GenBank Accession No. M63974 (1991).
GenBank Accession No. M63975 (1991).
GenBank Accession No. M63976 (1991).
GenBank Accession No. M63977 (1991).
GenBank Accession No. M63978 (1991).
GenBank Accession No. M27281 (1990).
GenBank Accession No. X04571 (1995).
GenBank Accession No. X63556 (1997).
GenBank Accession No. L19896 (1994).
GenBank Accession No. L04947 (1995).
GenBank Accession No. M16237 (1995).
GenBank Accession No. M16243 (1995).
GenBank Accession No. M16244 (1995).
GenBank Accession No. M16245 (1995).
GenBank Accession No. K03212 (1995).
GenBank Accession No. K03213 (1995).
GenBank Accession No. K03214 (1995).
GenBank Accession No. K03215 (1995).
GenBank Accession No. K03216 (1995).
GenBank Accession No. K03217 (1995).
GenBank Accession No. K03218 (1995).
GenBank Accession No. M13994 (1994).
GenBank Accession No. M13995 (1994).
GenBank Accession No. L22473 (1993).
GenBank Accession No. L22474 (1993).
GenBank Accession No. AJ000185 (1998).
International Search Report, Application No. PCT/US99/05021.
International Search Report, Application No. PCT/US94/05291.
Achen, et al., Proc. Natl. Acad. Sci. (USA), 95(2): 548-553 (1998).
Andersson et al., J. Biol. Chem., 267(16):11260-11266 (1992).
Aprelikova et al., Cancer Research, 52:746-748 (1992).
Bell et al., Nucl. Acids Res., 14(21):8427-8446 (1986).
Berse et al., Mol. Biol. Cell. 3:211-220 (1992).
Anderson, W.F. (1992) Science 256:808-813.
Friedman, T. (1992) Nat. Genetics 2:93-98.
Williams, R.S. (1993) Am. J. Med. Sci. 306:129-136.
Hockel et al. (1993) Arch. Surg. 128:423-429.
Guzman et al. (1993) Circ. Res. 73:1202-1207.
Andersson W.F., "Human gene therapy," *Science*, 256:808-813 (1992).
Friedman, T., "A brief history of gene therapy," *Nat. Genetics*, 2:93-98 (1992).
Williams, R.S. "Southwestern internal medicine conference: prospects for gene therapy of ischemic heart disease," *Am. J. Med. Sci.*, 306(2): 129-136 (1993).
Hockel et al., "Therapeutic angiogenesis,"*Arch. Surg.*, 128:423-429 (1993).
Guzman et al. "Efficient gene transfer into myocardium by direct injection of adenovirus vectors," *Circ. Res.*, 73:1202-1207 (1993).
Bellomo et al., "Mice Lacking the Vascular Endothelial Growth Factor-B Gene (Vegfb) Have Smaller Hearts, Dysfunctional Coronary Vasculature, and Impaired Recovery From Cardiac Ischemia," *Circ. Research*, 89(2): e29-e35 (2000).

Cockerill et al., "Angiogenesis: Models and Modulators" *Intl. Rev. Cytology*, 159:113-160 (1995).

Gamble et al., "Regulation of In Vitro Capillary Tube Formation by Anti-Integrin Antibodies," *J. Cell. Bio.*, 121(4): 931-943 (1993).

Goldspiel et al., "Human Gene Therapy," *Clinical Pharmacy*, 12: 488-505 (1993).

Grimmond et al., "Cloning and Charaterization of a Novel Human Gene Related to Vascular Endothelial Growth Factor," *Genome Research*, 6:124-131 (1996).

Hyde et al., "Correction of the ion transport defect in cystic fibrosis transgenic mice by gene therapy," *Nature*, 362: 250-255 (1993).

Kay et al., "In Vivo Gene Therapy of Hemophilia B: Sustained Partial Correction in Factor LX-Deficient Dogs," *Science*, 262:117-119 (1993).

Kolodka et al., "Hepatic Gene Therapy: Efficient Retroviral-Mediated Gene Transfer into Rat Hepatocytes in Vivo," *Somatic Cell and Molecular Genetics*, 19(5): 491-497 (1993).

Shibuya et al., "Nucleotide sequence and expression of a novel human receptor-type tyrosine kinase gene *(flt)* closley related to the *fms* family," *Oncogene*, 519-524 (1990).

Silins et al., "Analysis of the Promoter Region of the Human VEGF-Related Factor Gene," *Biochem. Biophys. Res. Comm.*, 230: 413-418 (1997).

Stewart et al., "Insulin delivery by somatic cell gene therapy," *J of Mol. Endocrinology*, 11: 335-341 (1993).

Townson et al., "Characterization of the Murine VEGF-Related Factor Gene," *Biochem. & Biophys. Res. Comms.*,220: 922-928 (1996).

Yang et al., "Flk-1, a Receptor for Vascular Endothelial Growth Factor (VEGF), Is Rxpressed by Retinal Progenitor Cells," *J. Neuroscience*, 16(19):6089-6099 (Oct. 1, 1996).

Supplementary European Search Report, Application No. EP 02 72 6730, mailed Oct. 25, 2004.

Supplementary European Search Report, Application No. EP 00 90 5992, mailed Nov. 8, 2004.

Litwin et al., "Role of Cytokines in Endothelial Cell Functions," *Human Cytokines* 101-129 (1995).

Walsh et al., "Gene Therapy for Human Hemoglobinopathies," P.S.E.B.M. 204: 289-300 (1993).

Alderson, R.F., et al., "Vascular Endothelial Cell Growth Factor (VEGF)-2 Enhances the Development of Rat Photoreceptor Cells In Vitro," *Keystone Symposia, Ocular Cell & Molec. Biol.*, p. 32, Abstract No. 202, Association for Research in Vision and Ophthalmology (Feb. 1999).

Alshuler, D., et al., "Taurine promotes the differentiation of a vertebrate retinal cell type in vitro," *Development* 119:1317-1328, The Company of Biologists Limited (Dec. 1993).

Better, M., et al., "*Escherichia coli* Secretion of an Active Chimeric Antibody Fragment," *Science* 240:1041-1043, American Association for the Advancement of Science (1988).

Böcker-Meffert, S., et al., "Erythropoietin and VEGF Promote Neural Outgrowth from Retinal Explants in Postnatal Rats," *Invest. Ophthalmol. Vis. Sci.* 43:2021-2026, Association for Research in Vision and Ophthalmology (Jun. 2002).

Colwell, D.E., et al., "Method for Generating a High Frequency of Hybridomas Producing Monoclonal IgA Antibodies," *Meth. Enzymol.* 121:42-51, Academic Press, Inc. (1986).

Danis, R.P., et al., "Anti-angiogenic therapy of proliferative diabetic retinopathy," *Esp. Opin. Pharma.* 2:395-407, Ashley Publications Ltd. (Mar. 2001).

Eichmann, A., et al., "Avain VEGF-C: cloning, embryonic expression pattern and stimulation of the differentiation of VEGFR2-expressing endothelial cell precursors," *Development* 125:743-752, The Company of Biologists Limited (Feb. 1998).

Enholm, B., et al., "Vascular endothelial Growth Factor-C: A Growth factor for Lymphatic and bloodVascular Endothelial Cells," *Trends Cardiovasc. Med.* 8:292-297, Elsevier Science Inc. (Oct. 1998).

Ferrara, N., et al., "The Vascular Endothelial Growth Factor Family of Polypeptides," *J. Cell. Biochem.* 47:211-218, Wiley-Liss, Inc. (1991).

Ferra, N., "Vascular Endothelial Growth factor and the Regulation of Angiogensis," *Recent Prog. Hormone Res.* 55:15-36, The Endocrine Society (Mar. 2000).

George, D. G., et al., "Chap. 12. Current Methods on Sequence Comparison and Analysis," in: *Macromolecular Sequencing and Synthesis, Selected Methods and Applications*, Schlesinger, A.M., ed., John Wiley & Sons, Inc., Hoboken, NJ, pp. 127-149 (1988).

Gerhardinger, C., et al., "Expression of Vascular Endothelial growth Factor in the Human Retina and in Nonproliferative Diabetic Retinopathy," *Am. J. Pathol.* 152:1453-1462, American Society for Investigative Pathology (Jun. 1998).

Halin, C. and Neri, D., "Antibody-Based Targeting of Angiogensis," *Crit. Rev. Ther. Drug Carrier Syst.* 18:299-339, Begell House, Inc. (Aug. 2001).

Hannink, M., et al., "Deletions in the C-Terminal Coding Region of the v-sis Gene: Dimerization Is Required for Transformation," *Molec. Cell. Biol.* 6:1304-1314, American Society for Microbiology (1986).

Hirai, M., et al., "Expression of Vascular Endothlial Growth Factors (VEGF-A/VEGF-1 and VEGF-C/VEGF-2) in Postmenopausal Uterine Endometrial Carcinoma," *Gynecol. Oncol.* 80:181-188, Academic Press (Feb. 2001).

Houck, K.A., et al., "The Vascular endothelial Growth Factor Family: Identification of a Fourth Molecular Species and Characterization of Alternative Splicing of RNA," *Molec. Endocrinol.* 5:1806-1814, Williams & Wilkins (1991).

Joosten, V., "The production of antibody fragments and antibody fusion proteins by yeasts and filamentous fungi," *Microbial Cell factories* 2:1-15, BioMed Central (Jan. 2003).

Kelley, M.W., et al., "Regulation of Proliferation and Photoreceptor Differentiation in Fetal Human Retinal Cerll cultures," *Invest. Ophthalmol. Vis. Sci.* 36:1280-1289, Association for research in Vision and Ophthalmology (Jun. 1995).

Longo, R., et al., "Anti-angiogenic therapy: Rationale, challenges and clinical studies," *Angiogenesis* 5:237-256, Kluwer Academic Publishers (De. 2002).

Ngo, J.T., et al., "Computational complexity, Protein Structure Prediction, and the Levinthal Paradox," *The Protein Folding Problem and Tertiary Structure Prediction*, Merz, Jr., K. and Le Grand, S., eds., Birjhauser, Boston, MA, pp. 491-495 (Jan. 1994).

Pajusola, K., et al., "FLT4 receptor tyrosine kinase contains seven immunoglobulin-like loops and is expressed in multiple human tissues and cell lines," *Cancer Res.* 52:5738-5743, American Association for Cancer Research (1992).

Pajusola, K., et al., "Two human FLT4 receptor tyrosine kinase isoforms with distinct carboxy terminal tails are producted by alternative processing of primary transcripts," *Oncogene* 8:2931-2937, Nature Publishing Group (Nov. 1993).

Rudikoff, S., et al., "Single amino acid substitution altering antigen-binding specificity," *Proc. Natl. Acad. Sci. USA* 79:1979-1983, National Academy of Sciences (1982).

Schlaeppi, J.-M,. et al., "Characterization of a new potent, in vivo neutralizing monoclonal antibody to human vascular endothelial growth factor," *J. cancer Res. clin. Oncol.* 125:336-342, Springer-Verlag (May 1999).

Schratzbrger, P., et al., "Reversal of experimental diabetic neuropathy b VEGF gene transfer," *J. Clin. Invest.* 107:1083-1092, American Societies for clincal Investigation (May 2000).

Schulz-Key, S., et al., "Ciliary Neurotrophic Factor as a Transient Negative Regulator of Rod Development in Rat Retina, " *Invest. Ophthalmol. Vis. Sci.* 43:3099-308, Association for Research in Vision and Ophthalmology (Sep. 2002).

Seigel, G.M., "The golden age of retinal cell culture," *Molec. Vis.* 5:4, Molecular Vision (Apr. 1999).

Skerra, A., and Plückthun, A., "Assembly of a Functional Immunoglobulin $F_v$Fragment in *Escherichia coli,*" *Science* 240:1038-1041, Americn Association for the Advancement of Science (1998).

Stacker, S.A. and Achen, M.G., "The Vascular Endothelial Growth Factor Family: Signalling for Vascular Development," *Growth Factors* 17:1-11, Hardwood Academic Publishers (Mar. 1999).

Tischer, E., et al., "Vascualar Endothelial Growth Factor: A New Member of the Platelet-Derived Growth Factor Gene Family," *Biochem. Biophys. Res. Commun.* 165.1198-1206, Academic Press, Inc. (1989).

Vale, P.R., et al., "Percutaneous Electromechanical Mapping Demostrates Efficacy of pVGI.1(VEGF2) in an Animal Model of Chronic Myocardial Ischemia," *Circulation Suppl.* 100:I.22, Abstract No. 109, American Heart Association Inc. (Nov. 1999).

Vale, P.R., et al., "Randomized, Single-Blind, Placebo-Conrolled Pilot Study of catheter-Based Myocardial Gene Transfer for Therapeutic Angiogenesis using Left Ventricular Electromechanical Mapping in Patients With Chronic Myocardial Ischemia," *Circulation* 103:2138-2143, American Heart Association Inc. (May 2001).

van der Flier, M., et al., "Antibody neutralization of vascular endothlial growth factor (VEGF) fails to attenuate vascular permeability and brain edema in experimental pneumococcal meningitis," *J. Neuroimmunol.*160:170-177, Elsevier B.V. (Mar. 2005).

Verma, I.M. and Somia, N., "Gene therapy - promises, problems and prospects," *Nature* 389:239-242, Macmillan Publishers Ltd. (Sep. 1997).

Walsh, D.A., "Angiogenesis and arthritis," *Rheumatology*38:103-112, British Society for Rheumatology (Feb. 1999).

Winkler, K., et al., "Changing the Antigen Binding Specificity by Single Point Mutations of an Anti-p24 (HIV-1) Antibody," *J. Immunol.* 165:4505-4514, The American Association of Immunologists (Oct. 2000).

Yourey, P.A., et al., "Vascular Endothelial Cell Growth Factors Promote the In Vitro Development of Rat Photoreceptor Cells," *J. Neurosci.* 20:6781-6788, Society for Neuroscience (Sep. 2000).

Yourey, P.A., et al., "Vascular Endothelial Cell Growth Factors Promote the In Vitro Development of Rat Photorecptor Cels," *Molec. Biol. Cell.* 10:39a, Abstract No. 227, American Society for Microbiology (Nov. 1999) and 39th Ann. Meeting of the American Society of Cell Biology, Washington, DC, held Dec. 1999).

NCBI Entrez, Accession No. AF010302, Mandriota S.J. and Pepper, M.S. (first available and last update 1997).

NCBI Entrez, Accessio No. S08167, Paulsson, G. et al. (first available 1993 and last update Mar. 2005).

NCBI Entrez, Accession No. AAW27553, Han. Z. (first available Feb. 2005 and last updated Sep. 2005.

Dialog File 351, Accession No. 12299390, WPI English language abstract of WO 98/55619 (Document FP6 listed on accompanying SB/08A).

Breier, G., et al., "Expression of vascular endothelial growth factor during embryonic angiogenesis and endothelial cell differentiation," *Development* 114:521-532, The Company of Biologists Limited (1992).

Borg, J.-P., et al., "Biochemical characterzation of two isoforms of FLT4, a VEGF receptor-related tyrosine kinase," *Oncogene* 10:973-984, Stockton Press (Mar. 1995).

Capogrossi, M.C., "Gene Therapy of Coronary Artery Disease," Project No. Z01 AG00811-01, Abstract (Jan. 1994).

Capogrossi, M.C., "Gene Therapy of Coronary Artery Disease," Project No. Z01 AG00811-02, Abstract (Jan. 1995).

Choi, I.H., et al., "Angiogenesis and Mineralization During Distraction Osteogenesis," *Korean Med. Sci.* 17:435-447, The Korean Academy of Medical Sciences (Aug. 2002).

Copy of declaration of Dr. Kari Alitalo, In re of: U.S. Appl. No. 08/585,895, Alitalo et al., filed Jan. 12, 1996, submitted Nov. 26, 1997.

Dias, S., et al., "Vascular endothelial growth factor (VEGF)-C signaling through FLT-4 (VEGFR-3) mediates leukemic cell proliferation, survival, and resistance to chemotherapy," *Blood* 99:2179-2184, The American Society of Hematology (Mar. 2002).

English language abstract of JP 64-38100 A, cited as document FP14 on Form PTO/SB/08A, Derwent Accession No. 1989-088700/198912.

English language abstract of JP 2-117698 A, cited as document FP15 on Form PTO/SB/08A, Derwent Accession No. 1990-181364/199024.

Fan, T.-P.D., et al., "Controlling the vascular: angiogenesis, anti-angiogenesis and vascular targeting of gene therapy," *Trends Pharmaco. Sci.* 16:57-66, Elsevier Science Ltd. (Feb. 1995).

Isner, J.M., et al. "Arterial Gene Therapy for Therapeutic Angiogenesis in patients With Peripheral Artery Disease," *Circulation* 91:2687-2692, American Heart Association, Inc. (Jun. 1995).

Isner, J.M. and Feldman, L.J., "Gene therapy for arterial disease," *Lancet* 344:1653-1654, The Lancet Ltd. (Dec. 1994).

Isner, J.M., et al., "Physiologic Assessment of Angiogenesis by Arterial Gene Therapy with Vascular Endothelial Growth Factor," *J. Cell. Biochem. (Suppl.* 21A):378, Abstract C6-215, Wiley-Liss (Mar.-Apr. 1995).

Isner, J.M., "Therapeutic Angiogenesis in Vascular Medicine," Project No. R01 HL53354-01, Abstract (Mar. 1995).

Kubo, H., et al., "Blockade of vascular endothelial growth factor receptor-3 signaling inhibits fibroblasts growth factor-2-included lymphangiogenesis in mouse cornea," *Proc. Natl. Acad. Sci.* 99:8868-8873, The National Academy of Sciences (Jun. 2002).

Kuzuya, M. and Kinsella, J.L., "Induction of Endothelial cell Differentiation in vitro by Fibroblast-Derived Soluble Factors," *Exp. Cell Res.* 215:310-318, Academic Press, Inc. (Dec. 1994).

Maher, P.A., "Stimulation of Endothelial cell Proliferation by Vanadate Is Specific for Microvascular Endothelial Cells," *J. Cel. Physiol.* 151:549-554, Wiley-Liss, Inc. (1992).

Mesri, E.A., et al., "Expression of Vascular Endothelial Growth Factor From a defective Herpes Simplex Virus Type 1 Amplicon Vector Induces Angiogenesis in Mice," *Circulation Res.* 76:161-167, American Heart Association, Inc. (Feb. 1995).

Mühlhauser, J., et al., "In Vivo Gene Transfer into Porcine cardiac cells with a Replication-Deficient Recombinant Adenovirus Vector," *Circulation* 88:I-475, Abstract No. 2558, American Heart Association (Oct. 1993).

Mühlhauser, J., et al., "VEGF$_{165}$ expressed by a Replication-Deficient Recombinant Adenovirus Vector Induces Angiogenesis In Vivo," *Circulation Res.* 77:1077-1086, American Heart Association, Inc (Dec. 1995).

Oikawa, T., et al., "Three Isoforms of Platelet-Derived growth Factors All Have the capability to Induce Angiogenesis In Vivo," *Biol. Pharm. Bull.* 17:1686-1688, (Dec. 1994).

Pajusola, K., et al., "Signaling properties of FLT4, a propteolytically processed receptor tyrosine kinase related to two VEGF receptors," *Oncogene* 9:3545-3555, Stockton Press Ltd. (Dec. 1994).

Pepper, M.S., et al., "In Vitro Angiogenic and Proteolytic Properties of Bovine Lymphatic Endothelial Cells," *Exp. Cell Res.* 210:298-305, Academic Press, Inc. (Jan. 1994).

Plate, K.H., "From angiogenesis to lymphangiogenesis," *Nat. Med.* 7:151-152, Nature America, Inc. (Feb. 2001).

Spranger, J. and Pfeiffer, A.F.H., "New concepts in pathogenesis and treatment of diabetic retinopathy," *Exp. Clin. Endocrinol. Diabetes 109(Suppl. 2)*:S438-S450, J.A. Barth Verlag (2001).

Stacker, S.A. and Achen, M.G., "The Vascular Endothelial Growth Factor Family: Signalling for Vascular Development," *Growth Factors* 17:1-11, Taylor & Francis (1999).

Symes, J.F. and Sniderman, A.D., "Angiogenesis: potential therapy for ischaemic disease," *Curr. Opin. Lipidol.* 5:305-312, Current Science Ltd. (Aug. 1994).

Takeshita, S., et al., "*In Vivo* Evidence of Enhanced Angiogenesis Following Direct Arterial Gene Transfer of the Plasmid Encoding Vascular Endothelial Growth factor," *Circulation* 88:I-476, Abstract No. 2565, American Heart Association (Oct. 1993).

Takeshita, S., et al., "Therapeutic Angiogenesis. A Single Intraarterial Bolus of Vascular Endothelial Growth Factor Augments Revascularization in a Rabbit Ischemic Hind Limb Model," *J. Clin. Invest.* 93:662-670, The American Society for Clinical Investigation, Inc. (Feb. 1994).

Walsh, D.A. and Pearson, C.I., "Angiogenesis in the pathogenesis of inflammatory joint and lung diseases," *Arthritis Res.* 3:147-153, BioNed Central Ltd. (Feb. 2001).

Williams, R.S., "Southwestern Internal Medicine Conference: Prospects for gene Therapy of Ischemic Heart Disease," *Am. J. Med. Sci.* 306:129-136, Lippincott Williams & Wilkins (Aug. 1993).

Witzenbichler, B., et al., "Vascular Endothelial Growth Factor-C (VEGF-C/VEGF-2) Promotes Angiogenesis in the Setting of Tissue Ischemia," *Am. J. Pathol.* 153:381-394, American Society for Investigative Pathology, Inc. (Aug. 1998).

Yeung, P.K.F., "VEGF-2," *Curr. Opin. Invest. Drugs* 2:796-800, PharmaPress Ltd. (Jun. 2001).

Anderson, W.F., "Human gene therapy," *Nature* 392:25-30, Macmillan Magazines ltd. (Apr. 1998).

Maynard, J. and Georgiou, G., "antibody Engineering," *Annu. Rev. Biomed. Eng.* 2:339-376, Annual Reviews (Aug. 2000).

Morea, V., et al., "Antibody Modeling: Implications for Engineering and Design," *Methods* 20:267-279, Academic Press (Mar. 2000).

Letter from John J. Chicca II, Ph.D., Molecular Diagnostic Services, Inc. regarding a third progress report for a project entitled "Cloning and expression of VEGF-2 gene and efficacy of VEGF-2 protein utilizing the 3-D collagen angiogenesis assay and proliferation," dated Feb. 16, 2006.

Letter from John J. chicca II, Ph.D., Moleculat Diagnostic Services, Inc. regarding a fourth progree report for a project entitled "Cloning and expression of VEGF-2 gene and the efficacy of VEGF-2 protein utilizing the 3-D collagen angiogenesis assay and proliferation," dated Mar. 14, 2006.

\* cited by examiner

FIG. 1A

```
361  AGATCTTGAAAAGTATTGATAATGAGTGGAGAAAGACTCAATGCATGCCACGGGAGGTGT
     ----+----|----+----|----+----|----+----|----+----|----+----|  420
     TCTAGAACTTTTCATAACTATTACTCACCTCTTTCTGAGTTACGTACGGTGCCCTCCACA
      I  L  K  S  I  D  N  E  W  R  K  T  Q  C  M  P  R  E  V  C

421  GTATAGATGTGGGGAAGGAGTTTGGAGTCGCGACAAACACCTTCTTTAAACCTCCATGTG
     ----+----|----+----|----+----|----+----|----+----|----+----|  480
     CATATCTACACCCCTTCCTCAAACCTCAGCGCTGTTTGTGGAAGAAATTTGGAGGTACAC
      I  D  V  G  K  E  F  G  V  A  T  N  T  F  F  K  P  P  C  V

481  TGTCCGTCTACAGATGTGGGGTTGCTGCAATAGTGAGGGGCTGCAGTGCATGAACACCA
     ----+----|----+----|----+----|----+----|----+----|----+----|  540
     ACAGGCAGATGTCTACACCCCAACGACGTTATCACTCCCCGACGTCACGTACTTGTGGT
      S  V  Y  R  C  G  G  C  C  N  S  E  G  L  Q  C  M  N  T  S

541  GCACGAGCTACCTCAGCAAGACGTTATTTGAAATTACAGTGCCTCTCTCTCAAGGCCCCA
     ----+----|----+----|----+----|----+----|----+----|----+----|  600
     CGTGCTCGATGGAGTCGTTCTGCAATAAACTTTAATGTCACGGAGAGAGTTCCGGGGT
      T  S  Y  L  S  K  T  L  F  E  I  T  V  P  L  S  Q  G  P  K

601  AACCAGTAACAATCAGTTTTGCCAATCACACTTCCTGCCGATGCATGTCTAAACTGGATG
     ----+----|----+----|----+----|----+----|----+----|----+----|  660
     TTGGTCATTGTTAGTCAAAACGGTTAGTGTGAAGGACGGCTACGTACAGATTTGACCTAC
      P  V  T  I  S  F  A  N  H  T  S  C  R  C  M  S  K  L  D  V
```

FIG. 1B

```
661  TTTACAGACAAGTTCATTCCATTATTAGACGTTCCCTGCCAGCAACACTACCACAGTGTC
     ----+----|----+----|----+----|----+----|----+----|----+----|  720
     AAATGTCTGTTCAAGTAAGGTAATAATCTGCAAGGACGGTCGTTGTGATGGTGTCACAG
      Y  R  Q  V  H  S  I  R  R  S  L  P  A  T  L  P  Q  C  Q

721  AGGCAGCGGAACAAGACCTGCCCCACCAATTACATGTGGAATAATCACATCTGCAGATGCC
     ----+----|----+----|----+----|----+----|----+----|----+----|  780
     TCCGTCGCTTGTTCTGGACGGGGTGGTTAATGTACACCTTATTAGTGTAGACGTCTACGG
      A  A  N  K  T  C  P  T  N  Y  M  W  N  N  H  I  C  R  C  L

781  TGGCTCAGGAAGATTTATGTTTTCCTCGGATGCTGGAGATGACTCAACAGATGGATTCC
     ----+----|----+----|----+----|----+----|----+----|----+----|  840
     ACCGAGTCCTTCTAAATACAAAAGGAGCCTACGACCTCTACTGAGTTGTCTACCTAAGG
      A  Q  E  D  F  M  F  S  S  D  A  G  D  D  S  T  D  G  F  H

841  ATGACATCTGTGGACCAAAACAAGGAGCTGGATGAAGAGACCTGTCAGTGTGTCTGCAGAG
     ----+----|----+----|----+----|----+----|----+----|----+----|  900
     TACTGTAGACACCTGGTTTGTTCCTCGACCTACTTCTCTGGACAGTCACACAGACGTCTC
      D  I  C  G  P  N  K  E  L  D  E  E  T  C  Q  C  V  C  R  A

901  CGGGGCTTCGGCCTGCCTGCCAGCTGTGGACCCCCACAAAGAACTAGACAGAAACTCATGCCAGT
     ----+----|----+----|----+----|----+----|----+----|----+----|  960
     GCCCCGAAGCCGGACGGTCGACACCTGGGGTGTTTCTTGATCTGTCTTTGAGTACGGTCA
      G  L  R  P  A  S  C  G  P  H  K  E  L  D  R  N  S  Q  C
```

```
      GTGTCTGTAAAAACAAACTCTTCCCCAGCCAATGTGGGGCCAACCGAGAATTTGATGAAA
      ----------+---------+---------+---------+---------+---------+   1020
      CACAGACATTTTGTTTGTGAGAAGGGGTCGGTTACACCCCGGTTGGCTCTTAAACTACTTT
961     V  C  K  N  K  L  F  P  S  Q  Q  C  G  A  N  R  E  F  D  E  N

ACACATGCCAGTGTGTATGTAAAAGAACCTGCCCCCAGAAATCAACCCCTAAATCCTGGAA
      ----------+---------+---------+---------+---------+---------+   1080
      TGTGTACGGTCACACATACATTTTCTTGGACGGGGTCTTTAGTTGGGATTTAGGACCTT
1021    T  C  Q  C  V  C  K  R  T  C  P  R  N  Q  P  L  N  P  G  K

AATGTGCCTGTGAATGTACAGAAAGTCCACAGAAATGCTTGTTAAAAGGAAAGAAGTTCC
      ----------+---------+---------+---------+---------+---------+   1140
      TTACACGGACACTTACATGTCTTTCAGGTGTCTTTACGAACAATTTTCCTTTCTTCAAGG
1081    C  A  C  E  C  T  E  S  P  Q  K  C  L  L  K  G  K  K  F  H

ACCACCAAACATGCAGCTGTTACAGACGGCCATGTACGAACCGCCAGAAGGCTTGTGAGC
      ----------+---------+---------+---------+---------+---------+   1200
      TGGTGGTTTGTACGTCGACAATGTCTGCCGGTACATGCTTGGCGGTCTTCCGAACACTCG
1141    H  Q  T  C  S  C  Y  R  R  P  C  T  N  R  Q  K  A  C  E  P

CAGGATTTTCATATAGTGAAGAAGTGTGTCGTTGTGTCCCTTCATATTGGCAAAGACCAC
      ----------+---------+---------+---------+---------+---------+   1260
      GTCCTAAAAGTATATCACTTCTTCACACAGCAACACAGGAAGTATAACCGTTTCTGGTG
1201    G  F  S  Y  S  E  E  V  C  R  C  V  P  S  Y  W  Q  R  P  Q
```

```
1261  AAATGAGCTAAGATTGTACTGTTTTCCAGTTCATCGATTTTCTATTATGGAAAACTGTGT
      ----+----+----+----+----+----+----+----+----+----+----+----+  1320
      TTTACTCGATTCTAACATGACAAAAGGTCAAGTAGCTAAAAGATAATACCTTTTGACACA
              M  S  *

1321  TGCCACAGTAGAACTGTCTGTGAACAGAGAGACCCTTGTGGGTCCATGCTAACAAAGACA
      ----+----+----+----+----+----+----+----+----+----+----+----+  1380
      ACGGTGTCATCTTGACAGACACTTGTCTCTCTGGGAACACCCAGTACGATTGTTTCTGT

1381  AAAGTCTGTCTTTCCTGAACCATGTGGATAACTTTACAGAAATGGACTGGAGCTCATCTG
      ----+----+----+----+----+----+----+----+----+----+----+----+  1440
      TTTCAGACAGAAAGGACTTGGTACACCTATTGAAATGTCTTTACCTGACCTCGAGTAGAC

1441  CAAAAGGCCCTCTTGTAAAGACTGGTTTTCTGCCAATGACCAAACAGCCAAGATTTCCTC
      ----+----+----+----+----+----+----+----+----+----+----+----+  1500
      GTTTTCCGGAGAACATTTCTGACCAAAAGACGGTTACTGGTTGTGCGGTTCTAAAAGGAG

1501  TTGTGATTTCTTTAAAAGAATGACTATATAATTTATTTCCACTAAAAATATTGTTTCTGC
      ----+----+----+----+----+----+----+----+----+----+----+----+  1560
      AACACTAAAGAAATTTTCTTACTGATATATTAAATAAAGGTGATTTTTATAACAAAGACG

1561  ATTCATTTTTATAGCAACAACAATTGGTAAAACTCACTGTGATCAATATTTTATATCAT
      ----+----+----+----+----+----+----+----+----+----+----+----+  1620
      TAAGTAAAAAATATCGTTGTTGTTAACCATTTGAGTGACACTAGTTATAAAATATAGTA

1621  GCAAAATATGTTTAAAATAAAATGAAAATTGTATTTATAAAAAAAAAAAAAA
      ----+----+----+----+----+----+----+----+----+----+----  1674
      CGTTTTATACAAATTTTATTTTACTTTTAACATAAATATTTTTTTTTTTTTTT
```

FIG. 1E

```
  1   CGAGGCCACGGCTTATGCAAGCAAAGATCTGGAGGAGCAGTTACGGTCTGTGTCCAGTGT
      ------------+------------+------------+------------+------------+------------+
                                            M  T  V  L  Y  P  E  Y  W  K  M  Y  K  C  Q  L  R

71   AGATGAACTCATGACTGTACTCTACCAGAATATTGGAAAATGTACAAGTGTCAGCTAAG
      ------------+------------+------------+------------+------------+------------+
                                            K  G  G  W  Q  H  N  R  E  Q  A  N  L  N  S  R  T  E  E  T

121   GAAAGGAGGCTGGCAACATAACAGAGACAGGCCAACCTCAACTCAAGGACAGAAGAGAC
      ------------+------------+------------+------------+------------+------------+
                                            I  K  F  A  A  A  H  Y  N  T  E  I  L  K  S  I  D  N  E  W

181   TATAAAATTTGCTGCAGCACATTATAATACAGAGATCTTGAAAAGTATTGATAATGAGTG
      ------------+------------+------------+------------+------------+------------+
                                            I  K  F  A  A  A  H  Y  N  T  E  I  L  K  S  I  D  N  E  W

241   GAGAAAGACTCAATGCATGCCACGGGAGTGTGTATAGATGTGGGGAAGGAGTTTGGAGT
      ------------+------------+------------+------------+------------+------------+
                                            R  K  T  Q  C  M  P  R  E  V  C  I  D  V  G  K  E  F  G  V

301   CGCGACAAACACCTTCTTTAAACCTCCATGTGTTCCGTCTACAGATGTGGGGTTGCTG
      ------------+------------+------------+------------+------------+------------+
                                            A  T  N  T  F  F  K  P  P  C  V  S  V  Y  R  C  G  G  C
```

FIG. 2A

```
361  CAATAGTGAGGGGCTGCAGTGCATGAACACCAGCACGAGCTACCTCAGCAAGACGTTATT
     ------+---------+---------+---------+---------+---------+
      N  S  E  G  L  Q  C  M  N  T  S  T  S  Y  L  S  K  T  L  F

421  TGAAATTACAGTGCCTCTCTCTCAAGGCCCCAAACAGTAACAATCAGTTTTGCCAATCA
     ------+---------+---------+---------+---------+---------+
      E  I  T  V  P  L  S  Q  G  P  K  P  V  T  I  S  F  A  N  H

481  CACTTCCTGCCGATGCATGTCTAAACTGGATGTTTACAGACAAGTTCATTCCATTATTAG
     ------+---------+---------+---------+---------+---------+
      T  S  C  R  C  M  S  K  L  D  V  Y  R  Q  V  H  S  I  I  R

541  ACGTTCCCTGCCAGCAACACTACCACAGTGTCAGGCAGCGAACAAGACCTGCCCCACCAA
     ------+---------+---------+---------+---------+---------+
      R  S  L  P  A  T  L  P  Q  C  Q  A  A  N  K  T  C  P  T  N

601  TTACATGTGGAATAATCACATCTGCAGATGCCTGGCTCAGGAAGATTTTATGTTTTCCTC
     ------+---------+---------+---------+---------+---------+
      Y  M  W  N  N  H  I  C  R  C  L  A  Q  E  D  F  M  F  S  S

661  GGATGCTGGAGATGACTCAACAGATGGATTCCATGACATCTGTGGACCAAACAAGGAGCT
     ------+---------+---------+---------+---------+---------+
      D  A  G  D  D  S  T  D  G  F  H  D  I  C  G  P  N  K  E  L
```

FIG. 2B

```
721  GGATGAAGAGACCTGTCAGTGTGTCTGCAGAGCGGGGCTTCGGCCTGCCAGCTGTGGACC
      D  E  E  T  C  Q  C  V  C  R  A  G  L  R  P  A  S  C  G  P

781  CCACAAAGAACTAGACAGAAACTCATGCCAGTGTGTCTGTAAAAACAAACTCTTCCCCAG
      H  K  E  L  D  R  N  S  C  Q  C  V  C  K  N  K  L  F  P  S

841  CCAATGTGGGGCCAACCGAGAATTTGATGAAAACACATGCCAGTGTGTATGTAAAAGAAC
      Q  C  G  A  N  R  E  F  D  E  N  T  C  Q  C  V  C  K  R  T

901  CTGCCCCAGAAATCAACCCCTAAATCCTGAAAATGTGCCCTGTGAATGTACAGAAAGTCC
      C  P  R  N  Q  P  L  N  P  G  K  C  A  C  E  C  T  E  S  P

961  ACAGAAATGCTTGTTAAAAGGAAAAGAAGTTCCACCACCAAACATGCAGCTGTTACAGACG
      Q  K  C  L  L  K  G  K  K  F  H  H  Q  T  C  S  C  Y  R  R

1021 GCCATGTACGAACCGCCAGAAGGCTTGTGAGCCAGGATTTTCATATAGTGAAGAAGTGTG
      P  C  T  N  R  Q  K  A  C  E  P  G  F  S  Y  S  E  E  V  C
```

FIG. 2C

```
1081  TCGTTGTGTCCCTTCATATTGGCAAAGACCACAAATGAGCTAAGATTGTACTGTTTCCA
      R  C  V  P  S  Y  W  Q  R  P  Q  M  S

1141  GTTCATCGATTTCTATTATGGAAACTGTGTTGCCACAGTAGAACTGTCTGTGAACAGA

1201  GAGACCCTTGTGGGTCCATGCTAACAAAGACAAAGTCTGTCTTTCCTGAACCATGTGGA

1261  TAACTTTACAGAAATGGACTGGAGCTCATCTGCAAAAGGCCTCTTGTAAAGACTGGTTT

1321  CTGCCAATGACCAAACAGCCAAGATTTCCTCTTGTGATTTCTTTAAAAGAATGACTATA

1381  TAATTTATTTCCACTAAAAATATGTTTCTGCATTCATTTTTATAGCAACAACAATTGGT

1441  AAAACTCACTGTGATCAATATTTTTATATCATGCAAAATATGTTTAAAATAAAATGAAAA

1501  TTGTATTATAAAAAAAAAAAAAAAAA
```

FIG. 2D

```
      1                                                                    50
Pdgfa  .MRTLACLLL LGCGYLAHVL AEEAEIPREV IERLARSQIH SIRDLQRLLE
Pdgfb  MNRCWA.LFL SLCCYLRLVS AEGDPIPEEL YEMLSDHSIR SFDDLQRLLH
Vegf   .....MNFLL SWVHWSLALL LY................ .LHHAKWSQA
Vegf2  ......MTV LYPEYWKMYK CQ................. .LRKGGWQHN 51                                                                  100
Pdgfa  IDSVGSEDSL DTSLRAHGVH ATKHVPEKRP LPIRRKRSI. ........
Pdgfb  GDP.GEEDGA ELDLNMTRSH SGGELES... .LARGRRSLG SLTIAEPAMI
Vegf   APMAE..... ......GGGQ NHHEVVKFMD .VYQR..... .....EEAVP
Vegf2  REQANLNSRT EETIKFAAAH YNTEILKSID NEWRK..... ..........

101                                                                  150
Pdgfa  AVCKTRTVIY EIPRSQVDPT SANFLIWPPC VEVKRCTGCC NTSSVKCQPS
Pdgfb  AECKTRTEVF EISRRLIDRT NANFLVWPPC VEVQRCSGCC NNRNVQCRPT
Vegf   SYCHPIETLV DIFQEYPDEI ..EYIFKPSC VPLMRCGGCC NDEGLEQVPT
Vegf2  TQCMPREVCI DVGKEFGVAT ..NTFFKPPC VSVYRCGGCC NSEGLQCMNT 151                                                                  200
Pdgfa  RVHHRSVKVA KVEYVRKKPK LKEVQVRLEE HLECAC.... AT........
Pdgfb  QVQLRPVQVR KIEIVRKKPI FKKATVTLED HLACKC.... ETVAAARPVT
Vegf   EESNITMQIM RIK.PH..QG QHIGEMSFLQ HNKCECRPKK DRARQEKKSV
Vegf2  STSYLSKTLF EIT.VPLSQG PKPVTISFAN HTSCRCMSKL DVYRQVHSII

FIG. 3A
```

```
         201                                                            250
Pdgfa        ...TSLNPD YREEDTDVR.  ........ ........ ........ ........
Pdgfb    RSPGGSQEQR AKTPQTRVTI RTVRVRRPPK GKHRKFKHTH DKTALKETLG
Vegf     GKCQKRKRK ........ ........ KSRYKSWSVY VGARCCLMPW SLPGPHP..
Vegf2    RRSLPATLPQ CQAANKTCPT NYMWNNHICR CLAQEDFMFS SDAGDDSTDG 251                                                            300
Pdgfa    ........ ........ ........ ........ ........ ........
Pdgfb    A....... ........ ........ ........ ........ ........
Vegf     ....CGP. ........ ........ ........ .CSE RRKHLFVQDP QTCKCSCKNT
Vegf2    FHDICGPNKE LDEETCQCVC RAGLRPASCG PHKEL...DR NSCQCVCKNK 301                                                            350
Pdgfa    ........ ........ ........ ........ ........ ........
Pdgfb    ........ ........ ........ ........ ........ ........
Vegf     .DSRCKARQ LELNERTCRC DKPRR... ........ ........ ........
Vegf2    LFPSQCGANR EFDENTCQC VCKRTCPRNQ PLNPGKCACE CTESPQKCLL 351                                                            398
Pdgfa    ........ ........ ........ ........ ........ ........
Pdgfb    ........ ........ ........ ........ ........ ........
Vegf     ........ ........ ........ ........ ........ ........
Vegf2    KGKKFHHQTC SCYRRPCTNR QKACEPGFSY SEEVCRCVPS YWQRPQMS
```

FIG. 3B

PERCENTAGE (%) OF AMINO ACID IDENTITIES BETWEEN
EACH PAIR OF GENES IS SHOWN IN THE
FOLLOWING TABLE

|        | PDGFα | PDGFβ | VEGF | VEGF-2 |
|--------|-------|-------|------|--------|
| PDGFα  |       |       |      |        |
| PDGFβ  | 48.0  |       |      |        |
| VEGF   | 20.7  | 22.7  |      |        |
| VEGF-2 | 28.5  | 22.4  | 30.0 |        |

FIG. 4

**Expression of VEGF2 mRNA
in Human Breast Tumor Cells**

Lane 1      Normal Tissue
Lane 2      Breast Tumor Tissue
Lanes 3-9   Breast Tumor Cell Lines Lane 1: 14-C and rainbow M.W. marker
Lane 2: FGF control
Lane 3: VEGF2 (M13-reverse & forward primer)
Lane 4: VEGF2 (M13-reverse & VEGF-F4 primer)
Lane 5: VEGF2 (M13-reverse & VEGF-F5 primer)

Lane M: Marker
Lane 1: Vector medium
Lane 2: VEGF2 medium

Lane M: Marker
Lane 1: vector cytoplasm
Lane 2: vector medium
Lane 3: VEGF2 cytoplasm
Lane 4: VEGF2 medium Lane 1: Molelukar weight marker
Lane 2: Precipitates containing VEGF2.

VASCULAR ENDOTHELIAL GROWTH FACTOR 2 AND METHODS OF USE

CROSS-REFERENCE TO RELATED APPLICATIONS

This application is a divisional of U.S. application Ser. No. 08/999,811, filed Dec. 24, 1997, now issued as U.S. Pat. No. 5,932,540, which is a continuation-in-part of both U.S. application Ser. No. 08/207,550, filed Mar. 8, 1994 now abandoned and U.S. application Ser. No. 08/465,968, filed Jun. 6, 1995, now issued as U.S. Pat. No. 6,608,182. The content of all the aforesaid applications are relied upon and incorporated by reference in their entirety.

BACKGROUND OF THE INVENTION

1. Field of the Invention

The present invention relates to newly identified polynucleotides, polypeptides encoded by such polynucleotides, the use of such polynucleotides and polypeptides, as well as the production of such polynucleotides and polypeptides. The polypeptides of the present invention have been identified as members of the vascular endothelial growth factor family. More particularly, the polypeptides of the present invention are human vascular endothelial growth factor 2 (VEGF2). The invention also relates to inhibiting the action of such polypeptides.

2. Related Art

The formation of new blood vessels, or angiogenesis, is essential for embryonic development, subsequent growth, and tissue repair. Angiogenesis is also an essential part of certain pathological conditions, such as neoplasia (i.e., tumors and gliomas). Abnormal angiogenesis is associated with other diseases such as inflammation, rheumatoid arthritis, psoriasis, and diabetic retinopathy (Folkman, J. and Klagsbrun, M., *Science* 235:442–447(1987)).

Both acidic and basic fibroblast growth factor molecules are mitogens for endothelial cells and other cell types. Angiotropin and angiogenin can induce angiogenesis, although their functions are unclear (Folkman, J., *Cancer Medicine, Lea and Febiger Press, pp.* 153–170 (1993)). A highly selective mitogen for vascular endothelial cells is vascular endothelial growth factor or VEGF (Ferrara, N. et al., *Endocr. Rev.* 13:19–32 (1992)), which is also known as vascular permeability factor (VPF).

Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifunctional regulator of endothelial cell growth and differentiation (Breier, G. et al., *Development* 114:521–532 (1992)).

VEGF shares sequence homology with human platelet-derived growth factors, PDGFα and PDGFβ (Leung, D. W., et al., *Science* 246:1306–1309, (1989)). The extent of homology is about 21% and 23%, respectively. Eight cysteine residues contributing to disulfide-bond formation are strictly conserved in these proteins. Although they are similar, there are specific differences between VEGF and PDGF. While PDGF is a major growth factor for connective tissue, VEGF is highly specific for endothelial cells. Alternatively spliced mRNAs have been identified for both VEGF, PLGF, and PDGF and these different splicing products differ in biological activity and in receptor-binding specificity. VEGF and PDGF function as homo-dimers or hetero-dimers and bind to receptors which elicit intrinsic tyrosine kinase activity following receptor dimerization.

VEGF has four different forms of 121, 165, 189 and 206 amino acids due to alternative splicing. VEGF 121 and VEGF 165 are soluble and are capable of promoting angiogenesis, whereas VEGF 189 and VEGF206 are bound to heparin containing proteoglycans in the cell surface. The temporal and spatial expression of VEGF has been correlated with physiological proliferation of the blood vessels (Gajdusek, C. M., and Carbon, S. J., *Cell Physiol.* 139: 570–579 (1989); McNeil, P. L., et al., *J. Cell. Biol.* 109: 811–822 (1989)). Its high affinity binding sites are localized only on endothelial cells in tissue sections (Jakeman, L. B., et al., *Clin. Invest.* 89:244–253 (1989)). The factor can be isolated from pituitary cells and several tumor cell lines, and has been implicated in some human gliomas (Plate, K. H., *Nature* 359:845–848 (1992)). Interestingly, expression of VEGF121 or VEGF 165 confers on Chinese hamster ovary cells the ability to form tumors in nude mice (Ferrara, N. et al., *J. Clin. Invest.* 91:160–170 (1993)). The inhibition of VEGF function by anti-VEGF monoclonal antibodies was shown to inhibit tumor growth in immune-deficient mice (Kim, K. J., *Nature* 362:841–844 (1993)). Further, a dominant-negative mutant of the VEGF receptor has been shown to inhibit growth of glioblastomas in mice.

Vascular permeability factor (VPF) has also been found to be responsible for persistent microvascular hyperpermeability to plasma proteins even after the cessation of injury, which is a characteristic feature of normal wound healing. This suggests that VPF is an important factor in wound healing. Brown, L. F. et al., *J. Exp. Med.* 176:1375–1379 (1992).

The expression of VEGF is high in vascularized tissues, (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sep. 30, 1992.

SUMMARY OF THE INVENTION

The polypeptides of the present invention have been putatively identified as a novel vascular endothelial growth factor based on amino acid sequence homology to human VEGF.

In accordance with one aspect of the present invention, there are provided novel mature polypeptides, as well as biologically active and diagnostically or therapeutically useful fragments, analogs, and derivatives thereof. The polypeptides of the present invention are of human origin.

In accordance with another aspect of the present invention, there are provided isolated nucleic acid molecules comprising polynucleotides encoding full length or truncated VEGF2 polypeptides having the amino acid sequences shown in SEQ ID NOS:2 or 4, respectively, or the amino acid sequences encoded by the cDNA clones deposited in bacterial hosts as ATCC Deposit Number 97149 on May 12, 1995 or ATCC Deposit Number 75698 on Mar. 4, 1994.

The present invention also relates to biologically active and diagnostically or therapeutically useful fragments, analogs, and derivatives of VEGF2.

In accordance with still another aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said proteins and subsequent recovery of said proteins.

In accordance with yet a further aspect of the present invention, there are provided processes for utilizing such polypeptides, or polynucleotides encoding such polypeptides for therapeutic purposes, for example, to stimulate angiogenesis, wound-healing, growth of damaged bone and tissue, and to promote vascular tissue repair.

In accordance with yet another aspect of the present invention, there are provided antibodies against such polypeptides and processes for producing such polypeptides.

In accordance with yet another aspect of the present invention, there are provided antagonists to such polypeptides, which may be used to inhibit the action of such polypeptides, for example, to prevent tumor angiogenesis and thus inhibit the growth of tumors, to treat diabetic retinopathy, inflammation, rheumatoid arthritis and psoriasis.

In accordance with another aspect of the present invention, there are provided nucleic acid probes comprising nucleic acid molecules of sufficient length to specifically hybridize to nucleic acid sequences of the present invention.

In accordance with another aspect of the present invention, there are provided methods of diagnosing diseases or a susceptibility to diseases related to mutations in nucleic acid sequences of the present invention and proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A–1E show the full length nucleotide (SEQ ID NO:1) and the deduced amino acid (SEQ ID NO:2) sequence of VEGF2. The polypeptide comprises approximately 419 amino acid residues of which approximately 23 represent the leader sequence. The standard one letter abbreviations for amino acids are used. Sequencing was performed using the Model 373 Automated DNA Sequencer (Applied Biosystems, Inc.). Sequencing accuracy is predicted to be greater than 97%.

FIGS. 2A–2D show the nucleotide (SEQ ID NO:3) and the deduced amino acid (SEQ ID NO:4) sequence of a truncated, biologically active form of VEGF2. The polypeptide comprises approximately 350 amino acid residues of which approximately the first 24 amino acids represent the leader sequence.

FIGS. 3A–3B are an illustration of the amino acid sequence homology between PDGFα (SEQ ID NO:5), PDGFβ (SEQ ID NO:6), VEGF (SEQ ID NO:7), and VEGF2 (SEQ ID NO:4). The boxed areas indicate the conserved sequences and the location of the eight conserved cysteine residues.

FIG. 4 shows, in table-form, the percent homology between PDGFα, PDGFβ, VEGF, and VEGF2.

DETAILED DESCRIPTION OF THE PREFERRED EMBODIMENTS

Figure 1A:
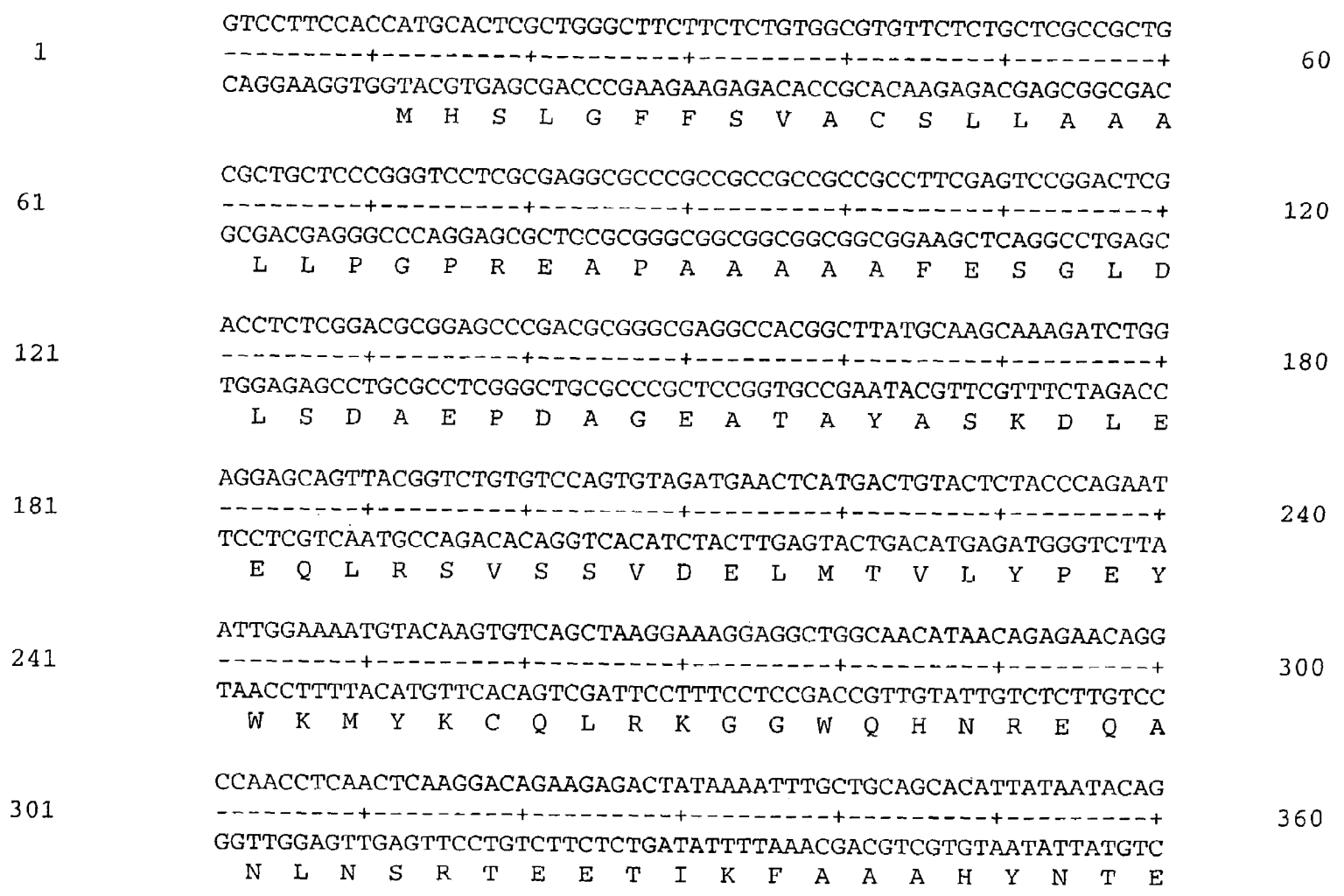
Figure 5:
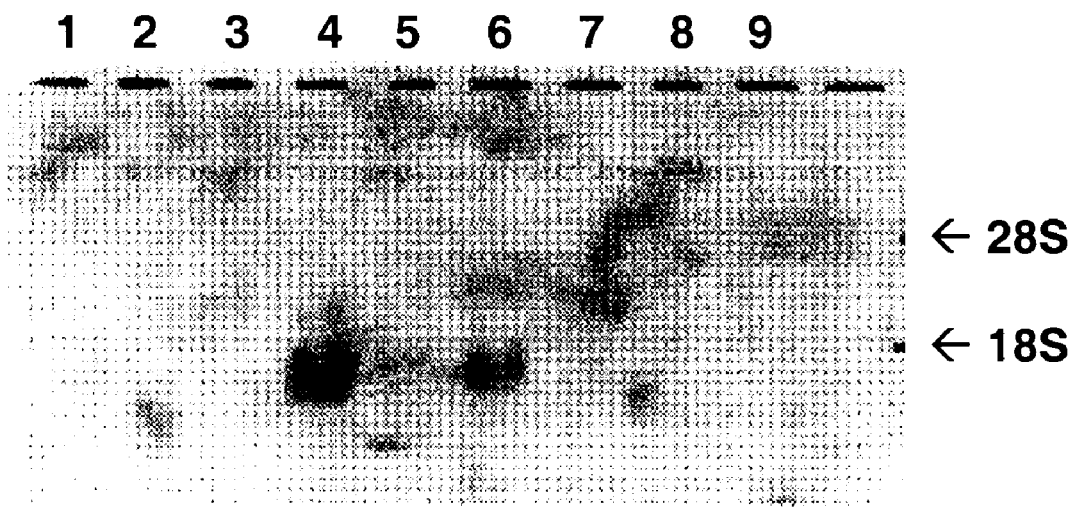
FIG. 5 shows the presence of VEGF2 mRNA in human breast tumor cell lines.

In accordance with one aspect of the present invention, there are provided isolated nucleic acid molecules comprising a polynucleotide encoding a VEGF2 polypeptide having the deduced amino acid sequence of FIG. 1 (SEQ ID NO:2), which was determined by sequencing a cloned cDNA. The nucleotide sequence shown in SEQ ID NO: 1 was obtained by sequencing a cDNA clone, which was deposited on May 12, 1995 at the American Type Tissue Collection (ATCC), 10801 University Boulevard, Manassas, Va. 20110-2209, and give ATCC Deposit No. 97149.

In accordance with another aspect of the present invention, there are provided isolated nucleic acid molecules comprising a polynucleotide encoding a truncated VEGF2 polypeptide having the deduced amino acid sequence of FIG. 2 (SEQ ID NO:4), which was determined by sequencing a cloned cDNA. The nucleotide sequence shown in SEQ ID NO:3 was obtained by sequencing a cDNA clone, which was deposited on Mar. 4, 1994 at the American Type Tissue Collection (ATCC), 10801 University Boulevard, Manassas, Va. 20110-2209, and ATCC Deposit Number 75698.

The deposited strains are maintained under the terms of the Budapest Treaty and will be made available to a patent office signatory to the Budapest Treaty.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 419 amino acid residues of which approximately the first 23 amino acid residues are the putative leader sequence such that the mature protein comprises 396 amino acids, and which protein exhibits the highest amino acid sequence homology to human vascular endothelial growth factor (30% identity), followed by PDGFα (24%) and PDGFβ (22%). (See FIG. 4). It is particularly important that all eight cysteines are conserved within all four members of the family (see boxed areas of FIG. 3). In addition, the signature for the PDGF/VEGF family, PXCVXXXRCXGCCN, (SEQ ID NO: 8) is conserved in VEGF2 (see FIG. 3). The homology between VEGF2, VEGF and the two PDGFs is at the protein sequence level. No nucleotide sequence homology can be detected, and therefore, it would be difficult to isolate the VEGF2 through simple approaches such as low stringency hybridization.

The VEGF2 polypeptide of the present invention is meant to include the full length polypeptide and polynucleotide sequence which encodes for any leader sequences and for active fragments of the full length polypeptide. Active fragments are meant to include any portions of the full length amino acid sequence which have less than the full 419 amino acids of the full length amino acid sequence as shown in SEQ ID NO:2, but still contain the eight cysteine residues shown conserved in FIG. 3 and that still have VEGF2 activity.

There are at least two alternatively spliced VEGF2 mRNA sequences present in normal tissues. The two bands in FIG. 7, lane 5 indicate the presence of the alternatively spliced mRNA encoding the VEGF2 polypeptide of the present invention.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or FIG. 2, or that of the deposited clones, or may be a different coding sequence which, as a result of the redundancy or degeneracy of the genetic code, encodes the same, mature polypeptide as the DNA of FIG. 1, FIG. 2, or the deposited cDNAs.

The polynucleotide which encodes for the mature polypeptide of FIG. 1 or FIG. 2 or for the mature polypeptides encoded by the deposited cDNAs may include: only the coding sequence for the mature polypeptide; the coding sequence for the mature polypeptide and additional coding sequences such as a leader or secretory sequence or a proprotein sequence; the coding sequence for the mature polypeptide (and optionally additional coding sequences) and non-coding sequences, such as introns or non-coding sequence 5' and/or 3' of the coding sequence for the mature polypeptide.

Thus, the term "polynucleotide encoding a polypeptide" encompasses a polynucleotide which includes only coding sequences for the polypeptide as well as a polynucleotide which includes additional coding and/or non-coding sequences.

The present invention further relates to variants of the hereinabove described polynucleotides which encode for fragments, analogs, and derivatives of the polypeptide having the deduced amino acid sequence of FIG. 1 or 2, or the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or 2 or the same mature polypeptide encoded by the cDNA of the deposited clones as well as variants of such polynucleotides which variants encode for a fragment, derivative, or analog of the polypeptides of FIG. 1 or 2, or the polypeptide encoded by the cDNA of the deposited clones. Such nucleotide variants include deletion variants, substitution variants, and addition or insertion variants.

As hereinabove indicated, the polynucleotide may have a coding sequence which is a naturally occurring allelic variant of the coding sequence shown in FIG. 1 or 2, or of the coding sequence of the deposited clones. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell 37:767 (1984)).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 396 in SEQ ID NO:2; (d) a nucleotide sequence encoding the polypeptide having the amino acid sequence encoded by the cDNA clone contained in ATCC Deposit No. 97149; (e) a nucleotide sequence encoding the mature VEGF2 polypeptide having the amino acid sequence encoded by the cDNA clone contained in ATCC Deposit No. 97149; or (f) a nucleotide sequence complementary to any of the nucleotide sequences in (a), (b), (c), (d), or (e).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:4; (b) a nucleotide sequence encoding the polypeptide having the amino acid sequence in SEQ ID NO:4, but lacking the N-terminal methionine; (c) a nucleotide sequence encoding the polypeptide having the amino acid sequence at positions from about 1 to about 326 in SEQ ID NO:4; (d) a nucleotide sequence encoding the polypeptide having the amino acid sequence encoded by the cDNA clone contained in ATCC Deposit No.75698; (e) a nucleotide sequence encoding the mature VEGF2 polypeptide having the amino acid sequence encoded by the cDNA clone contained in ATCC Deposit No.75698; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a VEGF2 polypeptide is intended that the nucleotide sequence of the polynucleotide is identical to the reference sequence except that the polynucleotide sequence may include up to five point mutations per each 100 nucleotides of the reference nucleotide sequence encoding the VEGF2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NOS: 1 or 3, or to the nucleotides sequence of the deposited cDNA clone(s) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The term "gene" means the segment of DNA involved in producing a polypeptide chain; it includes regions preceding and following the coding region (leader and trailer) as well as intervening sequences (introns) between individual coding segments (exons).

The present invention is further directed to fragments of the isolated nucleic acid molecules described herein. By a fragment of an isolated nucleic acid molecule having the nucleotide sequence of the deposited cDNA(s) or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–1500 nt in length are also useful according to the present invention as are fragments corresponding to most, if not all, of the nucleotide sequence of the deposited cDNA(s) or as shown in SEQ ID NO: 1 or SEQ ID NO:3. By a fragment at least 20 nt in length, for example, is intended fragments which include 20 or more contiguous bases from the nucleotide sequence of the deposited cDNA(s) or the nucleotide sequence as shown in SEQ ID NOS: 1 or 3.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to isolated nucleic acid molecules comprising polynucleotides which hybridize under stringent hybridization conditions to a portion of the polynucleotides in nucleic acid molecules of the invention described above, for instance, the cDNA clone(s) contained in ATCC Deposit Nos. 97149 or 75698. By "stringent hybridization conditions" is intended overnight overnight incubation at 42° C. in a solution comprising: 50% formamide, 5×SSC (750 mM NaCl, 75 mM trisodium citrate), 50 mL sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO: 1). Of course, a polynucleotide which hybridizes only to a poly A sequence (such as the 3' terminal poly(A) tract of the VEGF2 cDNA shown in SEQ ID NOS: 1 or 3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The present application is directed to nucleic acid molecules at least 95%, 96%, 97%, 98% or 99% identical to the nucleic acid sequence shown in SEQ ID NOS: 1 or 3 or to the nucleic acid sequence of the deposited cDNA(s), irrespective of whether they encode a polypeptide having VEGF2 activity. This is because even where a particular nucleic acid molecule does not encode a polypeptide having VEGF2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having VEGF2 activity include, inter alia, (1) isolating the VEGF2 gene or allelic variants thereof in a cDNA library; (2) in situ hybridization (e.g., "FISH") to metaphase chromosomal spreads to provide precise chromosomal location of the VEGF2 gene, as described in Verma et al., *Human Chromosomes: A Manual of Basic Techniques*, Pergamon Press, New York (1988); and Northern Blot analysis for detecting VEGF2 mRNA expression in specific tissues.

Preferred, however, are nucleic acid molecules having sequences at least 95%, 96%, 97%, 98% or 99% identical to a nucleic acid sequence shown in SEQ ID NOS: 1 or 3 or to a nucleic acid sequence of the deposited cDNA(s) which do, in fact, encode a polypeptide having VEGF2 protein activity. By "a polypeptide having VEGF2 activity" is intended polypeptides exhibiting VEGF2 activity in a particular biological assay. For example, VEGF2 protein activity can be measured using, for example, mitogenic assays and endothelial cell migration assays. See, e.g., Olofsson et al., *Proc. Natl. Acad. Sci. USA* 93:2576–2581 (1996) and Joukov et al., *EMBO J.* 5:290–298 (1996).

Of course, due to the degeneracy of the genetic code, one of ordinary skill in the art will immediately recognize that a large number of the nucleic acid molecules having a sequence at least 90%, 95%, 96%, 97%, 98%, or 99% identical to a nucleic acid sequence of the deposited cDNA(s) or the nucleic acid sequence shown in SEQ ID NO: 1 or SEQ ID NO:3 will encode a polypeptide "having VEGF2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having VEGF2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," Science 247:1306–1310 (1990), wherein the authors indicate that proteins are surprisingly tolerant of amino acid substitutions.

Thus, the present invention is directed to polynucleotides having at least a 70% identity, preferably at least 90% and more preferably at least a 95% identity to a polynucleotide which encodes the polypeptides of SEQ ID NOS:2 or 4, as well as fragments thereof, which fragments have at least 30 bases and preferably at least 50 bases and to polypeptides encoded by such polynucleotides.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to polypeptides which have the deduced amino acid sequence of FIG. 1 or 2, or which has the amino acid sequence encoded by the deposited cDNAs, as well as fragments, analogs, and derivatives of such polypeptides.

The terms "fragment," "derivative" and "analog" when referring to the polypeptide of FIG. 1 or 2 or that encoded by the deposited cDNA, means a polypeptide which retains the conserved motif of VEGF proteins as shown in FIG. 3 and essentially the same biological function or activity.

The polypeptides of the present invention may be recombinant polypeptides, natural polypeptides, or synthetic polypeptides, preferably recombinant polypeptides.

It will be recognized in the art that some amino acid sequences of the VEGF2 polypeptide can be varied without significant effect of the structure or function of the protein. If such differences in sequence are contemplated, it should be remembered that there will be critical areas on the protein which determine activity.

Thus, the invention further includes variations of the VEGF2 polypeptide which show substantial VEGF2 polypeptide activity or which include regions of VEGF2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragments, derivatives, or analogs of the polypeptides of FIG. 1 or 2, or that encoded by the deposited cDNAs may be: (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence; or (v) one in which comprises fewer amino acid residues shown in SEQ ID NOS: 2 or 4, and retains the conserved motif and yet still retains activity characteristics of the VEGF family of polypeptides. Such fragments, derivatives, and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the VEGF2 protein. The prevention of aggregation is highly desirable. Aggregation of proteins not only results in a loss of activity but can 110 also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the VEGF2 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the VEGF2 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224: 899–904 (1992) and de Vos et al. *Science* 255:306–312 (1992)).

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The polypeptides of the present invention include the polypeptides of SEQ ID NOS:2 and 4 (in particular the mature polypeptide) as well as polypeptides which have at least 70% similarity (preferably at least 70% identity) to the polypeptides of SEQ ID NOS:2 and 4, and more preferably at least 90% similarity (more preferably at least 95% identity) to the polypeptides of SEQ ID NOS:2 and 4, and still more preferably at least 95% similarity (still more preferably at least 90% identity) to the polypeptides of SEQ ID NOS:2 and 4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to recombinant vectors, which include the isolated nucleic acid molecules of the present invention, and to host cells containing the recombinant vectors, as well as to methods of making such vectors and host cells and for using them for production of VEGF2 polypeptides or peptides by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the VEGF2 genes of the invention. The culture conditions, such as temperature, pH and the like, are those previously used with the host cell selected for expression, and will be apparent to the skilled artisan.

The polynucleotides of the present invention may be employed for producing polypeptides by recombinant techniques. Thus, for example, the polynucleotide sequence may be included in any one of a variety of expression vectors for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain at least one selectable marker gene to provide a phenotypic trait for selection of transformed host cells. Such markers include dihydrofolate reductase (DHFR) or neomycin resistance for eukaryotic cell culture, and tetracycline or ampicillin resistance for culturing in *E. coli* and other bacteria.

The vector containing the appropriate DNA sequence as herein above described, as well as an appropriate promoter or control sequence, may be employed to transform an appropriate host to permit the host to express the protein. Representative examples of appropriate hosts, include but are not limited to: bacterial cells, such as *E. coli, Salmonella typhimurium,* and *Streptomyces*; fungal cells, such as yeast; insect cells, such as *Drosophila* S2 and *Spodoptera* Sf9; animal cells such as CHO, COS, and Bowes melanoma; and plant cells. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example—bacterial: pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Promoter regions can be selected from any desired gene using CAT (chloramphenicol transferase) vectors or other vectors with selectable markers.

Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, electroporation, transduction, infection, or other methods (Davis, L., et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., *Molecular Cloning: A Laboratory Manual*, Second Edition, Cold Spring Harbor Laboratory, Cold Spring Harbor, N.Y. (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers. Generally, recombinant expression vectors will include origins of replication and selectable markers permitting transformation of the host cell, e.g., the ampicillin resistance gene of *E. coli* and *S. cerevisiae* TRP 1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, well known to those skilled in the art, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

The polypeptides can be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1–5 mM) of calcium ion present during purification (Price et al, *J. Biol. Chem.* 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

Figure 12:
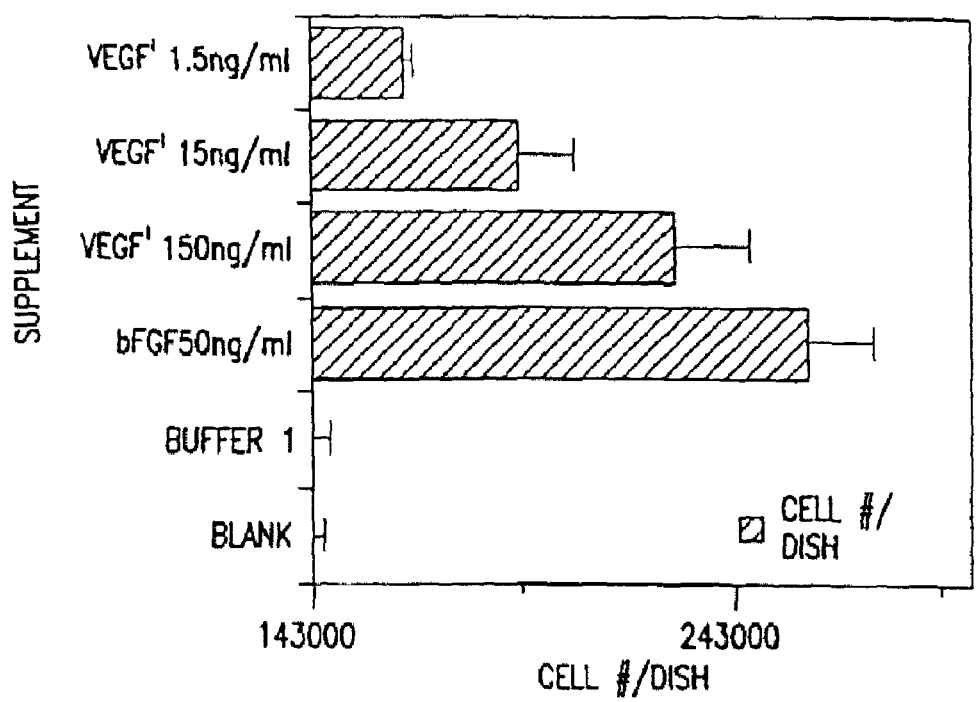
FIG. 12 is a bar graph illustrating the effect of partially-purified VEGF2 protein on the growth of vascular endothelial cells in comparison to basic fibroblast growth factor.
Figure 13:
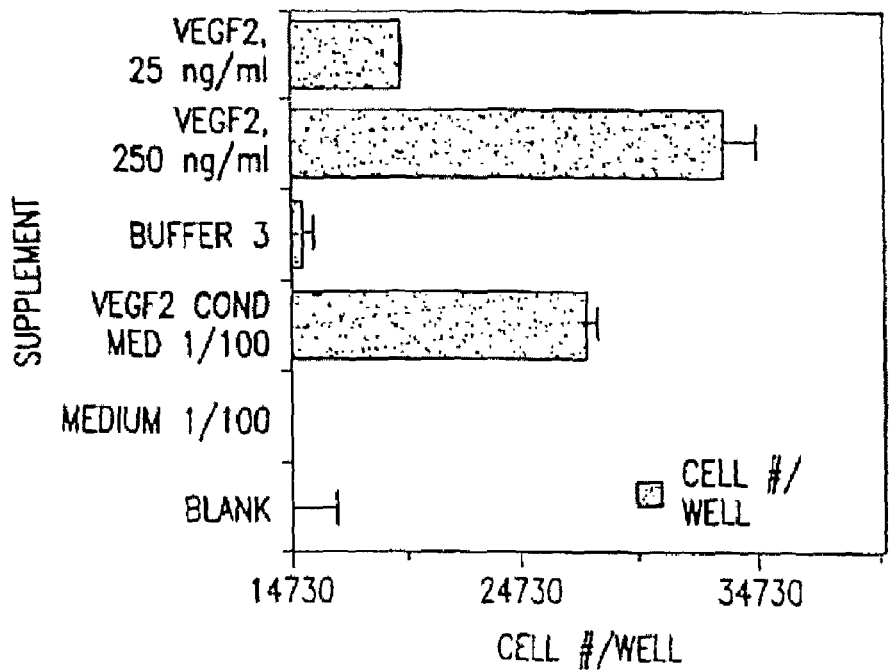
FIG. 13 is a bar graph illustrating the effect of purified VEGF2 protein on the growth of vascular endothelial cells.

As shown in FIGS. 12 and 13, the VEGF2 polypeptide of SEQ ID NO:2, minus the initial 46 amino acids, is a potent mitogen for vascular endothelial cells and stimulates their growth and proliferation. The results of a Northern blot analysis performed for the VEGF2 nucleic acid sequence encoding this polypeptide wherein 20 μg of RNA from several human tissues were probed with $^{32}$P-VEGF2, illustrates that this protein is actively expressed in the heart and lung which is further evidence of mitogenic activity.

Accordingly, VEGF2, or biologically active portions thereof, may be employed to promote angiogenesis, for example, to stimulate the growth of transplanted tissue where coronary bypass surgery is performed. VEGF2 may also be employed to promote wound healing, particularly to re-vascularize damaged tissues or stimulate collateral blood flow during ischemia and where new capillary angiogenesis is desired. VEGF2 may be employed to treat full-thickness wounds such as dermal ulcers, including pressure sores, venous ulcers, and diabetic ulcers. In addition, VEGF2 may be employed to treat full-thickness burns and injuries where a skin graft or flap is used to repair such burns and injuries. VEGF2 may also be employed for use in plastic surgery, for example, for the repair of lacerations, burns, or other trauma.

Along these same lines, VEGF2 may also be employed to induce the growth of damaged bone, periodontium or ligament tissue. VEGF2 may also be employed for regenerating supporting tissues of the teeth, including cementum and periodontal ligament, that have been damaged by, e.g., periodontal disease or trauma.

Since angiogenesis is important in keeping wounds clean and non-infected, VEGF2 may be employed in association with surgery and following the repair of cuts. It may also be employed for the treatment of abdominal wounds where there is a high risk of infection.

VEGF2 may be employed for the promotion of endothelialization in vascular graft surgery. In the case of vascular grafts using either transplanted or synthetic material, VEGF2 can be applied to the surface of the graft or at the junction to promote the growth of vascular endothelial cells. VEGF2 may also be employed to repair damage of myocardial tissue as a result of myocardial infarction. VEGF2 may also be employed to repair the cardiac vascular system after ischemia. VEGF2 may also be employed to treat damaged vascular tissue as a result of coronary artery disease and peripheral and CNS vascular disease.

VEGF2 may also be employed to coat artificial prostheses or natural organs which are to be transplanted in the body to minimize rejection of the transplanted material and to stimulate vascularization of the transplanted materials.

VEGF2 may also be employed for vascular tissue repair, for example, that occurring during arteriosclerosis and required following balloon angioplasty where vascular tissues are damaged.

VEGF2 nucleic acid sequences and VEGF2 polypeptides may also be employed for in vitro purposes related to scientific research, synthesis of DNA and manufacture of DNA vectors, and for the production of diagnostics and therapeutics to treat human disease. For example, VEGF2 may be employed for in vitro culturing of vascular endothelial cells, where it is added to the conditional medium in a concentration from 10 pg/ml to 10 ng/ml.

Fragments of the full length VEGF2 gene may be used as a hybridization probe for a cDNA library to isolate other genes which have a high sequence similarity to the gene or similar biological activity. Probes of this type generally have at least 50 base pairs, although they may have a greater number of bases. The probe may also be used to identify a cDNA clone corresponding to a full length transcript and a genomic clone or clones that contain the complete VEGF2 gene including regulatory and promotor regions, exons, and introns. An example of a screen comprises isolating the coding region of the VEGF2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides methods for identification of VEGF2 receptors. The gene encoding the receptor can be identified by numerous methods known to those of skill in the art, for example, ligand panning and FACS sorting (Coligan et al., *CurrentProtocols in Immun., I(2)*, Chapter 5, (1991)). Preferably, expression cloning is employed wherein polyadenylated RNA is prepared from a cell responsive to VEGF2, and a cDNA library created from this RNA is divided into pools and used to transfect COS cells or other cells that are not responsive to VEGF2. Transfected cells which are grown on glass slides are exposed to labeled VEGF2. VEGF2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VEGF2 can be photoaffinity linked with cell membrane or extract preparations that express the receptor molecule. Cross-linked material is resolved by PAGE and exposed to X-ray film. The labeled complex containing VEGF2 is then excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention is also related to a method of screening compounds to identify those which are VEGF2 agonists or antagonists. An example of such a method takes advantage of the ability of VEGF2 to significantly stimulate the proliferation of human endothelial cells in the presence of the comitogen Con A. Endothelial cells are obtained and cultured in 96-well flat-bottomed culture plates (Costar, Cambridge, Mass.) in a reaction mixture supplemented with Con-A (Calbiochem, La Jolla, Calif.). Con-A, polypeptides of the present invention and the compound to be screened are added. After incubation at 37° C., cultures are pulsed with 1%Ci of $^3$[H]thymidine (5 Ci/mmol; 1 Ci=37 BGq; NEN) for a sufficient time to incorporate the $^3$[H] and harvested onto glass fiber filters (Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]thymidine incorporation, as compared to a control assay where the compound is excluded, indicates stimulation of endothelial cell proliferation.

To assay for antagonists, the assay described above is performed and the ability of the compound to inhibit $^3$[H] thymidine incorporation in the presence of VEGF2 indicates that the compound is an antagonist to VEGF2. Alternatively, VEGF2 antagonists may be detected by combining VEGF2 and a potential antagonist with membrane-bound VEGF2 receptors or recombinant receptors under appropriate conditions for a competitive inhibition assay. VEGF2 can be labeled, such as by radioactivity, such that the number of VEGF2 molecules bound to the receptor can determine the effectiveness of the potential antagonist.

Alternatively, the response of a known second messenger system following interaction of VEGF2 and receptor would be measured and compared in the presence or absence of the compound. Such second messenger systems include but are not limited to, cAMP guanylate cyclase, ion channels or phosphoinositide hydrolysis. In another method, a mammalian cell or membrane preparation expressing the VEGF2 receptor is incubated with labeled VEGF2 in the presence of the compound. The ability of the compound to enhance or block this interaction could then be measured.

Potential VEGF2 antagonists include an antibody, or in some cases, an oligonucleotide, which bind to the polypeptide and effectively eliminate VEGF2 function. Alternatively, a potential antagonist may be a closely related protein which binds to VEGF2 receptors, however, they are inactive forms of the polypeptide and thereby prevent the action of VEGF2. Examples of these antagonists include a negative dominant mutant of the VEGF2 polypeptide, for example, one chain of the hetero-dimeric form of VEGF2 may be dominant and may be mutated such that biological activity is not retained. An example of a negative dominant mutant includes truncated versions of a dimeric VEGF2 which is capable of interacting with another dimer to form wild type VEGF2, however, the resulting homo-dimer is inactive and fails to exhibit characteristic VEGF activity.

Another potential VEGF2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., *Nucl. Acids Res.* 6:3073 (1979); Cooney et al., *Science* 241:456 (1988); and Dervan et al., *Science* 251:1360 (1991)), thereby preventing transcription and the production of VEGF2. The antisense RNA oligonucleotide hybridizes to the mRNA in vivo and blocks translation of the mRNA molecule into the VEGF2 polypeptide (Antisense—Okano, *J. Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of VEGF2.

Potential VEGF2 antagonists also include small molecules which bind to and occupy the active site of the polypeptide thereby making the catalytic site inaccessible to substrate such that normal biological activity is prevented. Examples of small molecules include but are not limited to small peptides or peptide-like molecules.

The antagonists may be employed to limit angiogenesis necessary for solid tumor metastasis. The identification of VEGF2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF2 is extremely low in normal tissues including breast, it can be found expressed at moderate levels in at least two breast tumor cell lines that are derived from malignant tumors. It is, therefore, possible that VEGF2 is involved in tumor angiogenesis and growth.

Gliomas are also a type of neoplasia which may be treated with the antagonists of the present invention.

The antagonists may also be used to treat chronic inflammation caused by increased vascular permeability. In addition to these disorders, the antagonists may also be employed to treat retinopathy associated with diabetes, rheumatoid arthritis and psoriasis.

The antagonists may be employed in a composition with a pharmaceutically acceptable carrier, e.g., as hereinafter described.

The VEGF2 polypeptides and agonists and antagonists may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the pharmaceutical compositions are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The VEGF2 polypeptides, and agonists or antagonists which are polypeptides may also be employed in accordance with the present invention by expression of such polypeptide in vivo, which is often referred to as "gene therapy."

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of a polypeptide in vivo, for example, by procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques* 7:980–990 (1989), or any other promoter (e.g., cellular promoters such as eukaryotic cellular promoters including, but not limited to, the histone, pol III, and α-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14×, VT-19-17-H2, ΨCRE, ΨCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the VEGF2 gene as part of a diagnostic assay for detecting diseases or susceptibility to diseases related to the presence of mutations in VEGF2 nucleic acid sequences.

Individuals carrying mutations in the VEGF2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature* 324:163–166 (1986)) prior to analysis. RNA or cDNA may also be used for the same purpose. As an example, PCR primers complementary to the nucleic acid encoding VEGF2 can be used to identify and analyze VEGF2 mutations. For example, deletions and insertions can be detected by a change in size of the amplified product in comparison to the normal genotype. Point mutations can be identified by hybridizing amplified DNA to radiolabeled VEGF2 RNA or alternatively, radiolabeled VEGF2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations may also be revealed by nuclease protection assays, such as RNase and S1 protection or the chemical cleavage method (e.g., Cotton et al., *PNAS, USA* 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis. The present invention also relates to a diagnostic assay for detecting altered levels of VEGF2 protein in various tissues since an over-expression of the proteins compared to normal control tissue samples may detect the presence of a disease or susceptibility to a disease, for example, abnormal cellular differentiation. Assays used to detect levels of VEGF2 protein in a sample derived from a host are well-known to those of skill in the art and include radioimmunoassays, competitive-binding assays, Western Blot analysis, ELISA assays and "sandwich" assay. An ELISA assay (Coligan et al., *Current Protocols in Immunology* 1(2), Chapter 6, (1991)) initially comprises preparing an antibody specific to the VEGF2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, such as, bovine serum albumen. Next, the monoclonal antibody is incubated in the dish during which time the monoclonal antibodies attach to any VEGF2 proteins attached to the polystyrene dish. All unbound monoclonal antibody is washed out with buffer. The reporter antibody linked to horseradish peroxidase is placed in the dish resulting in binding of the reporter antibody to any monoclonal antibody bound to VEGF2. Unattached reporter antibody is then washed out. Peroxidase substrates are then added to the dish and the amount of color developed in a given time period is a measurement of the amount of VEGF2 protein present in a given volume of patient sample when compared against a standard curve.

A competition assay may be employed wherein antibodies specific to VEGF2 are attached to a solid support. Polypeptides of the present invention are then labeled, for example, by radioactivity, and a sample derived from the host are passed over the solid support and the amount of label detected, for example by liquid scintillation chromatography, can be correlated to a quantity of VEGF2 in the sample.

A "sandwich" assay is similar to an ELISA assay. In a "sandwich" assay VEGF2 is passed over a solid support and binds to antibody attached to a solid support. A second antibody is then bound to the VEGF2. A third antibody which is labeled and specific to the second antibody is then passed over the solid support and binds to the second antibody and an amount can then be quantified.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with probes from the cDNA as short as 50 or 60 base pairs. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting VEGF2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al., *Nucl. Acids Res.* 6:3073 (1979); Cooney et al., *Science* 241:456 (1988); and Dervan et al. *Science,* 251:1360 (1991), thereby preventing transcription and the production of VEGF2. The antisense RNA oligonucleotide hybridizes to the mRNA in vivo and blocks translation of an mRNA molecule into the VEGF2 (antisense—Okano, *J. Neurochem.* 56:560 (1991); *Oligodeoxynucleotides as Antisense Inhibitors of Gene Expression*, CRC Press, Boca Raton, Fla. (1988)).

Alternatively, the oligonucleotides described above can be delivered to cells by procedures in the art such that the anti-sense RNA or DNA may be expressed in vivo to inhibit production of VEGF2 in the manner described above.

Antisense constructs to VEGF2, therefore, may inhibit the angiogenic activity of the VEGF2 and prevent the further growth or even regress solid tumors, since angiogenesis and neovascularization are essential steps in solid tumor growth. These antisense constructs may also be used to treat rheumatoid arthritis, psoriasis and diabetic retinopathy which are all characterized by abnormal angiogenesis.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256:495–497 (1975)), the trioma technique, the human B-cell hybridoma technique (Kozbor et al., *Immunology Today* 4:72 (1983)), and the EBV-hybridoma technique to produce human monoclonal antibodies (Cole et al., in *Monoclonal Antibodies and Cancer Therapy*, Alan R. Liss, Inc. (1985), pp. 77–96).

Techniques described for the production of single chain antibodies (U.S. Pat. No. 4,946,778) can be adapted to produce single chain antibodies to immunogenic polypeptide products of this invention.

Neutralization antibodies can be identified and applied to mask the vascular endothelial growth factor, and that has been shown in mice model systems against VEGF. VEGF2 can also be inactivated by certain dominant negative mutants within the gene itself. It is known that both PDGFα and β form either heterodimers or homodimers, and VEGF forms homodimers. Similar interaction between VEGF2 could be expected. These antibodies therefore may be used to block the angiogenic activity of VEGF2 and retard the growth of solid tumors. These antibodies may also be used to treat inflammation caused by the increased vascular permeability which results from the presence of VEGF2.

These antibodies may further be used in an immunoassay to detect the presence of tumors in certain individuals. Enzyme immunoassay can be performed from the blood sample of an individual. Elevated levels of of VEGF2 can be considered diagnostic of cancer.

The present invention is also directed to antagonist/inhibitors of the polypeptides of the present invention. The antagonist/inhibitors are those which inhibit or eliminate the function of the polypeptide.

Thus, for example, antagonists bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Truncated versions of VEGF2 can also be produced that are capable of interacting with wild type VEGF2 to form dimers that fail to activate endothelial cell growth, therefore inactivating the endogenous VEGF2. Or, mutant forms of VEGF2 form dimers themselves and occupy the ligand binding domain of the proper tyrosine kinase receptors on the target cell surface, but fail to activate cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF2 since receptor sites are occupied. In these ways, the action of the VEGF2 is prevented and the antagonist/inhibitors may be used therapeutically as an anti-tumor drug by occupying the receptor sites of tumors which are recognized by VEGF2 or by inactivating VEGF2 itself. The antagonist/inhibitors may also be used to prevent inflammation due to the increased vascular permeability action of VEGF2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a poly-acrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refer to either a single stranded polydeoxynucleotide or two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook et al., *Molecular Cloning: A Laboratory Manual*, Second Edition, Cold Spring Harbor Laboratory, Cold Spring Harbor, N.Y. (1989), p. 146). Unless otherwise provided, ligation may be accomplished using known buffers and conditions with 10 units of T4 DNA ligase ("ligase") per 0.5/g of approximately equimolar amounts of the DNA fragments to be ligated.

Unless otherwise stated, transformation was performed as described by the method of Graham, F. and Van der Eb, A., *Virology* 52:456–457 (1973).

EXAMPLE 1

Expression Pattern of VEGF2 in Human Tissues and Breast Cancer Cell Lines

Northern blot analysis was carried out to examine the levels of expression of VEGF2 in human tissues and breast cancer cell lines in human tissues. Total cellular RNA samples were isolated with RNAzol™ B system (Biotecx Laboratories, Inc.). About 10 μg of total RNA isolated from each breast tissue and cell line specified was separated on 1% agarose gel and blotted onto a nylon filter, (Sambrook et al., *Molecular Cloning: A Laboratory Manual*, Second Edition, Cold Spring Harbor Laboratory, Cold Spring Harbor, N.Y. (1989)). The labeling reaction was done according to the Stratagene Prime-It kit with 50 ng DNA fragment. The labeled DNA was purified with a Select-G-50 column from 5 Prime→3 Prime, Inc (Boulder, Colo.). The filter was then hybridized with a radioactive labeled full length VEGF2 gene at 1,000,000 cpm/ml in 0.5 M $NaPO_4$ and 7% SDS overnight at 65° C. After washing twice at room temperature and twice at 60° C. with 0.5×SSC, 0.1% SDS, the filters were then exposed at −70° C. overnight with an intensifying screen. A message of 1.6 Kb was observed in 2 breast cancer cell lines. FIG. 5, lane #4 represents a very tumorigenic cell line that is estrogen independent for growth.

Figure 6:
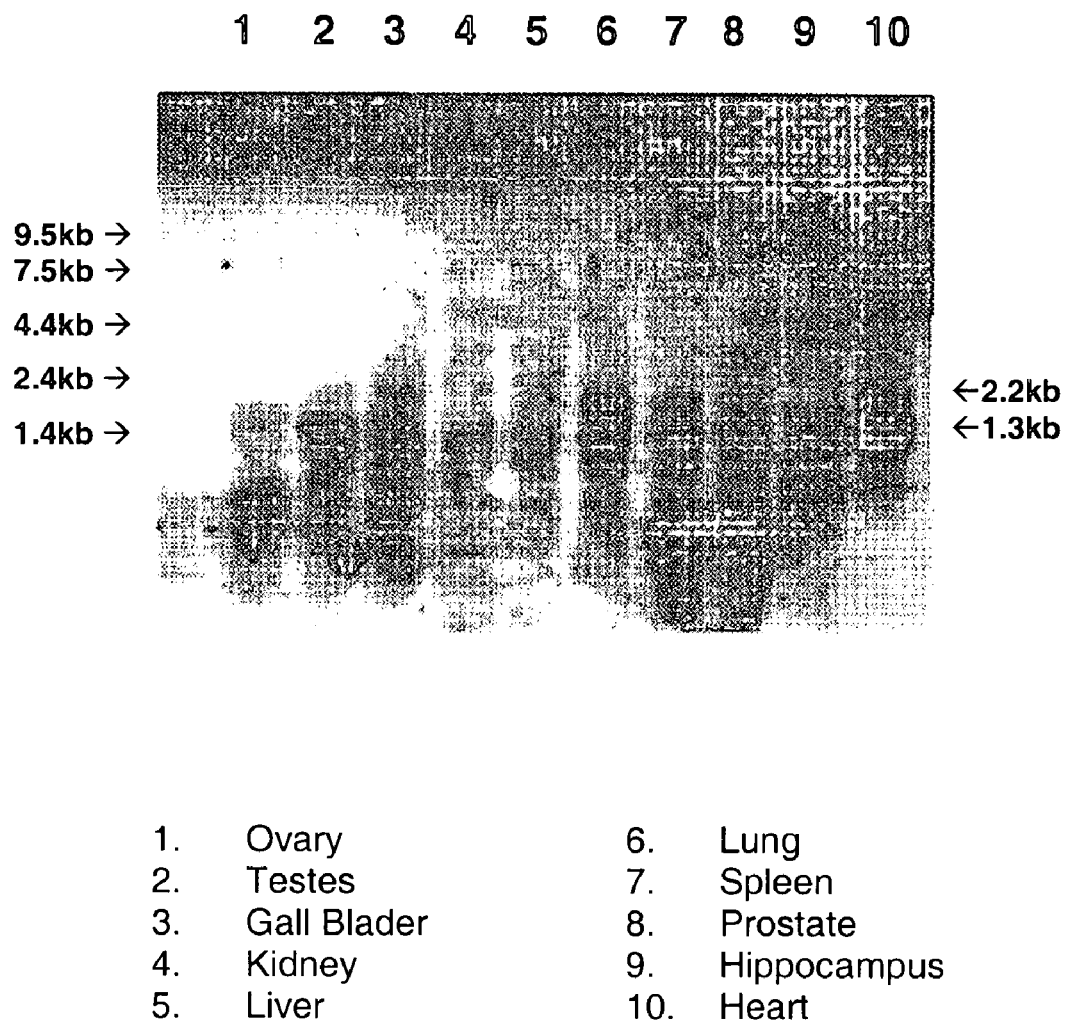
FIG. 6 depicts the results of a Northern blot analysis of VEGF2 in human adult tissues.

Also, 10/g of total RNA from 10 human adult tissues were separated on an agarose gel and blotted onto a nylon filter. The filter was then hybridized with radioactively labeled VEGF2 probe in 7% SDS, 0.5 M NaPO4, pH 7.2; 1% BSA overnight at 65° C. Following washing in 0.2×SSC at 65° C., the filter was exposed to film for 24 days at −70° C. with intensifying screen. See FIG. 6.

EXAMPLE 2

Expression of the Truncated Form of VEGF2 (SEQ ID NO:4) by in vitro Transcription and Translation The VEGF2 cDNA was transcribed and translated in vitro to determine the size of the translatable polypeptide encoded by the truncated form of VEGF2 and a partial VEGF2 cDNA. The two inserts of VEGF2 in the pBluescript SK vector were amplified by PCR with three pairs of primers, 1) M13-reverse and forward primers; 2) M13-reverse primer and VEGF primer F4; and 3) M13-reverse primer and VEGF primer F5. The sequence of these primers are as follows.

M13-2 Reverse Primer:
5'-ATGCTTCCGGCTCGTATG-3' (SEQ ID NO: 9)

This sequence is located upstream of the 5' end of the VEGF2 cDNA insert in the pBluescript vector and is in an anti-sense orientation as the cDNA. A T3 promoter sequence is located between this primer and the VEGF2 cDNA.

M13-2 Forward Primer:
5'GGGTTTTCCCAGTCACGAC-3' (SEQ ID NO: 10)

This sequence is located downstream of the 3' end of the VEGF2 cDNA insert in the pBluescript vector and is in an anti-sense orientation as the cDNA insert.

VEGF primer F4:
5'-CCACATGGTTCAGGAAAGACA-3' (SEQ ID NO: 11)

This sequence is located within the VEGF2 cDNA in an anti-sense orientation from bp 1259–1239, which is about 169 bp away from the 3' end of the stop codon and about 266 bp before the last nucleotide of the cDNA.

PCR reaction with all three pairs of primers produce amplified products with T3 promoter sequence in front of the cDNA insert. The first and third pairs of primers produce PCR products that encode the polypeptide of VEGF2 shown in SEQ ID NO:4. The second pair of primers produce PCR product that misses 36 amino acids coding sequence at the C-terminus of the VEGF2 polypeptide.

Approximately 0.5 µg of PCR product from first pair of primers, 1 µg from second pair of primers, 1 µg from third pair of primers were used for in vitro transcription/translation. The in vitro transcription/translation reaction was performed in a 25 µl of volume, using the $T_N T^{TM}$ Coupled Reticulocyte Lysate Systems (Promega, CAT# L4950). Specifically, the reaction contains 12.5 µl of TNT rabbit reticulocyte lysate 2 µl of TNT reaction buffer, 1 µl of T3 polymerase, 1 µl of 1 mM amino acid mixtrue (minus methionine), 4 µl of $^{35}$S-methionine (>1000 Ci/mmol, 10 mCi/ml), 1 µl of 40 U/ul; RNasin ribonuclease inhibitor, 0.5 or 1 µg of PCR products. Nuclease-free $H_2O$ was added to bring the volume to 25 µl. The reaction was incubated at 30° C. for 2 hours. Five microliters of the reaction product was analyzed on a 4–20% gradient SDS-PAGE gel. After fixing in 25% isopropanol and 10% acetic acid, the gel was dried and exposed to an X-ray film overnight at 70° C.

Figure 7:
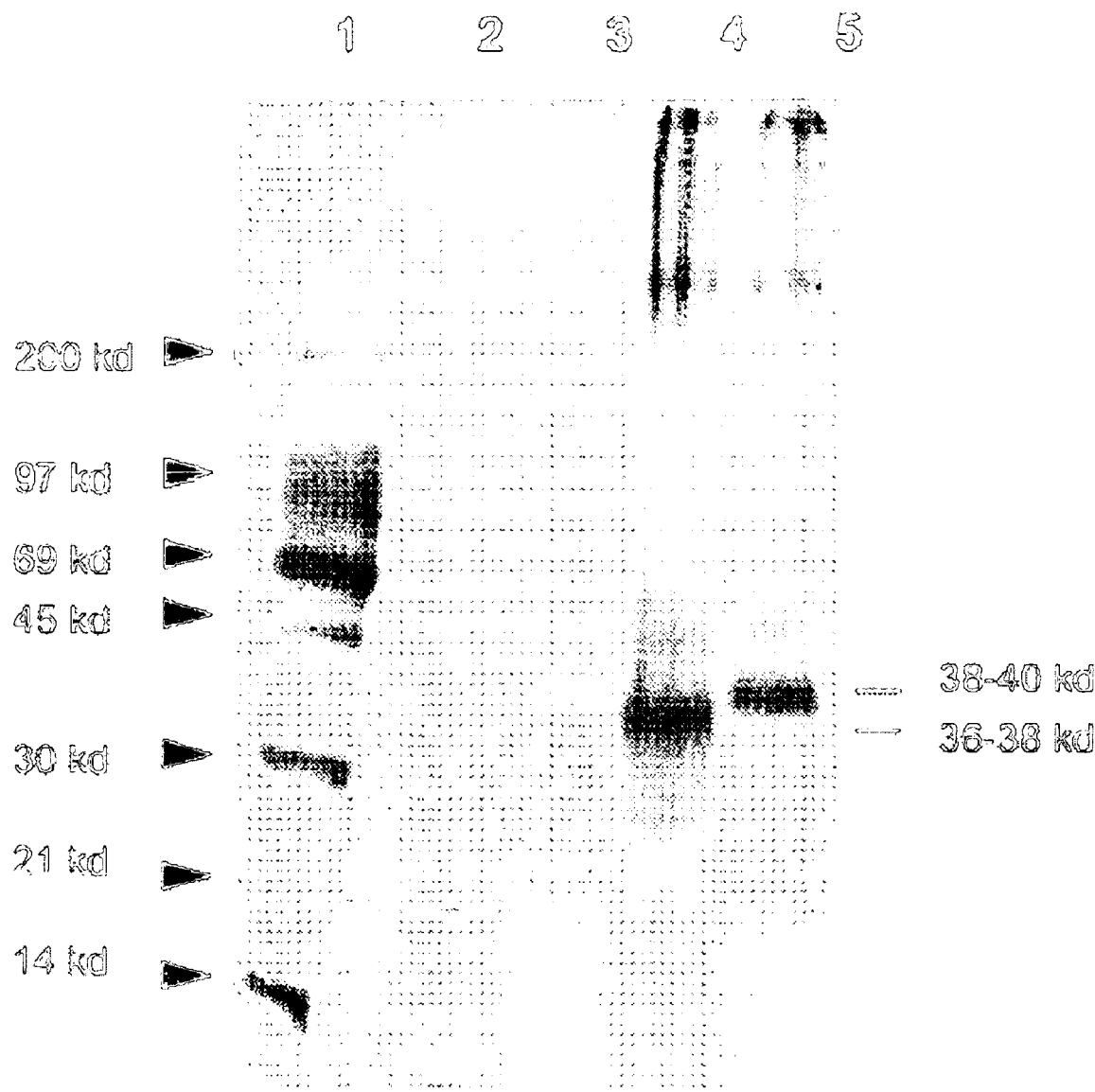
FIG. 7 shows a photograph of an SDS-PAGE gel after in vitro transcription, translation and electrophoresis of the polypeptide of the present invention. Lane 1: $^{14}C$ and rainbow M. W. marker; Lane 2: FGF control; Lane 3: VEGF2 produced by M13-reverse and forward primers; Lane 4: VEGF2 produced by M13 reverse and VEGF-F4 primers; Lane 5: VEGF2 produced by M13 reverse and VEGF-F5 primers.

As shown in FIG. 7, PCR products containing the truncated VEGF2 cDNA (i.e., as depicted in SEQ ID NO:3) and the cDNA missing 266 bp in the 3' un-translated region (3'-UTR) produced the same length of translated products, whose molecular weights are estimated to be 38–40 dk (lanes 1 and 3). The cDNA missing all the 3'UTR and missing sequence encoding the C-terminal 36 amino acids was translated into a polypeptide with an estimated molecular weight of 36–38 kd (lane 2).

EXAMPLE 3

Cloning and Expression of VEGF2 Using the Baculovirus Expression System

The DNA sequence encoding the VEGF2 protein without 46 amino acids at the N-terminus, see ATCC No. 97149, was amplified using PCR oligonucleotide primers corresponding to the 5' and 3' sequences of the gene:

The 5' primer has the sequence TGT AAT ACG ACT CAC TAT AGG GAT CCC GCC ATG GAG GCC ACG GCT TAT GC (SEQ ID NO:12) and contains a BamH1 restriction enzyme site (in bold) and 17 nucleotide nucleotide sequence complementary to the 5' sequence of VEGF2 (nt. 150–166).

The 3' primer has the sequence GATC TCT AGA TTA GCT CAT TTG TGG TCT (SEQ ID NO: 13) and contains the cleavage site for the restriction enzyme XbaI and 18 nucleotides complementary to the 3' sequence of VEGF2, including the stop codon and 15 nt sequence before stop codon.

The amplified sequences were isolated from a 1% agarose gel using a commercially available kit ("Geneclean," BIO 101, Inc., La Jolla, Calif.). The fragment was then digested with the endonuclease BamH1 and XbaI and then purified again on a 1% agarose gel. This fragment was ligated to pAcGP67A baculovirus transfer vector (Pharmingen) at the BamH1 and XbaI sites. Through this ligation, VEGF2 cDNA was cloned in frame with the signal sequence of baculovirus gp67 gene and was located at the 3' end of the signal sequence in the vector. This is designated pAcGP67A-VEGF2.

To clone VEGF2 with the signal sequence of gp67 gene to the pRG1 vector for expression, VEGF2 with the signal sequence and some upstream sequence were excised from the pAcGP67A-VEGF2 plasmid at the Xho restriction endonuclease site located upstream of the VEGF2 cDNA and at the XbaI restriction endonuclease site by XhoI and XbaI restriction enzyme. This fragment was separated from the rest of vector on a 1% agarose gel and was purified using "Geneclean" kit. It was designated F2.

The PRG1 vector (modification of pVL941 vector) is used for the expression of the VEGF2 protein using the baculovirus expression system (for review see: Summers, M. D. and Smith, G. E., "*A Manual of Methods for Baculovirus Vectors and Insect Cell Culture Procedures*," Texas Agricultural Experimental Station Bulletin No. 1555, (1987)). This expression vector contains the strong polyhedrin promoter of the *Autographa californica* nuclear polyhedrosis virus (AcMNPV) followed by the recognition sites for the restriction endonucleases BamH1, Sma1, XbaI, BglII and Asp718. A site for restriction endonuclease Xho1 is located upstream of BamH1 site. The sequence between Xho1 and BamHI is the same as that in PAcGp67A (static on tape) vector. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology 170:31–39 (1989).

The plasmid was digested with the restriction enzymes XboI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E coli* HB101 cells were then transformed and bacteria identified that contained the plasmid (pBac gp67-VEGF2) with the VEGF2 gene using the enzymes BamH1 and XbaI. The sequence of the cloned fragment was confirmed by DNA sequencing.

5 µg of the plasmid pBac gp67-VEGF2 was cotransfected with 1.0 µg of a commercially available linearized baculovirus ("BaculoGold™ baculovirus DNA", Pharmingen, San Diego, Calif.) using the lipofectin method (Felgner et al. Proc. Natl. Acad. Sci. USA, 84:7413–7417 (1987)).

1 µg of BaculoGold™ virus DNA and 5 µg of the plasmid pBac gp67-VEGF2 were mixed in a sterile well of a microtiter plate containing 50 PI of 1.0 serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith, supra. As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-gp67-VEGF2 at a multiplicity of infection (MOI) of 1. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

Figure 8A:
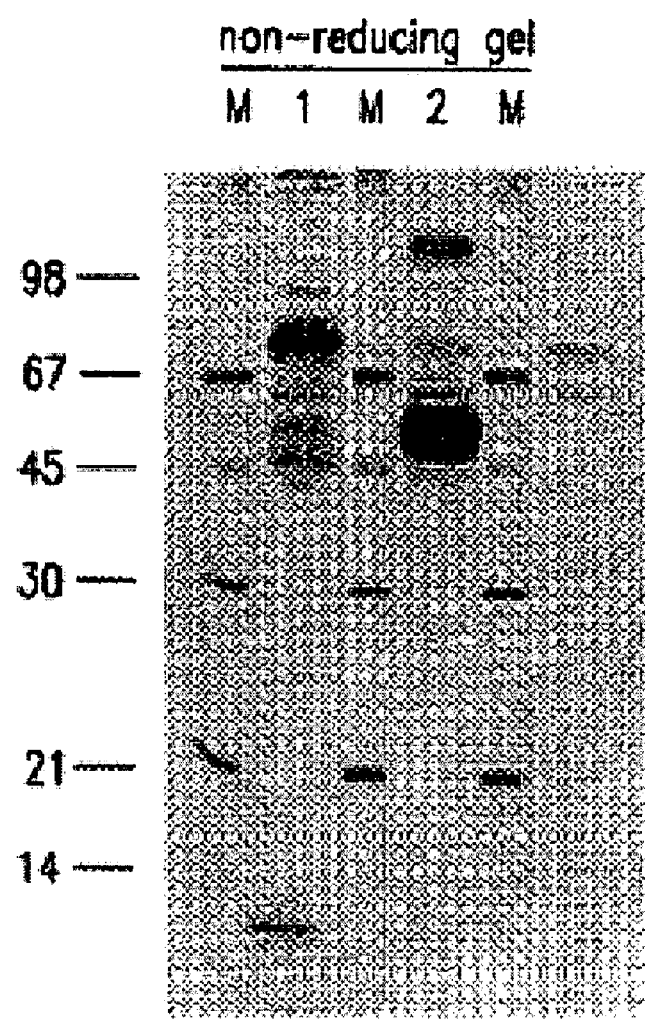
FIGS. 8A and 8B depict photographs of SDS-PAGE gels. VEGF2 polypeptide was expressed in a baculovirus system consisting of Sf9 cells. Protein from the medium and cytoplasm of cells were analyzed by SDS-PAGE under non-reducing (FIG. 8A) and reducing (FIG. 8B) conditions.
Figure 8B:
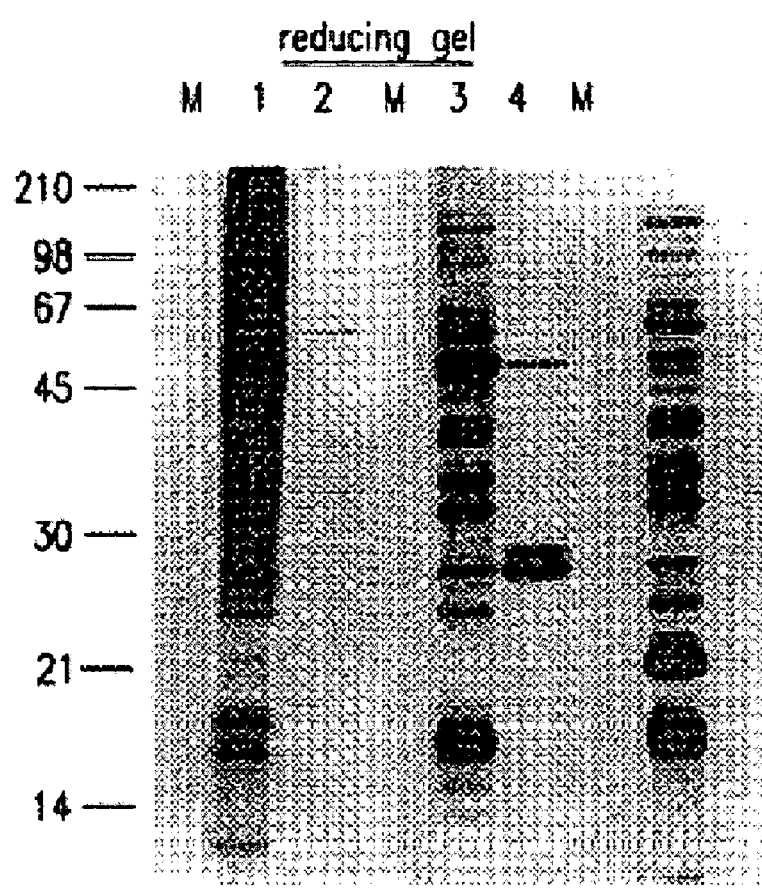
Figure 9:
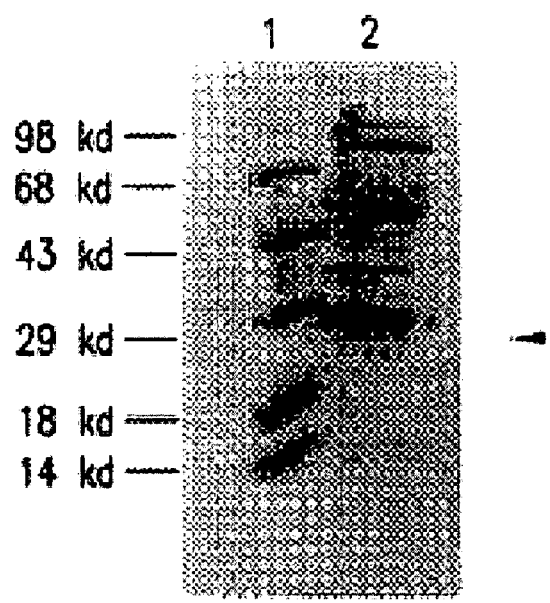
FIG. 9 depicts a photograph of an SDS-PAGE gel. The medium from Sf9 cells infected with a nucleic acid sequence of the present invention was precipitated. The resuspended precipitate was analyzed by SDS-PAGE and stained with coomassie brilliant blue.

Protein from the medium and cytoplasm of the Sf9 cells was analyzed by SDS-PAGE under non-reducing and reducing conditions. See FIGS. 8A and 8B, respectively. The medium was dialyzed against 50 mM MES, pH 5.8. Precipitates were obtained after dialysis and resuspended in 100 mM NaCitrate, pH 5.0. The resuspended precipitate was analyzed again by SDS-PAGE and was stained with Coomassie Brilliant Blue. See FIG. 9.

Figure 10:
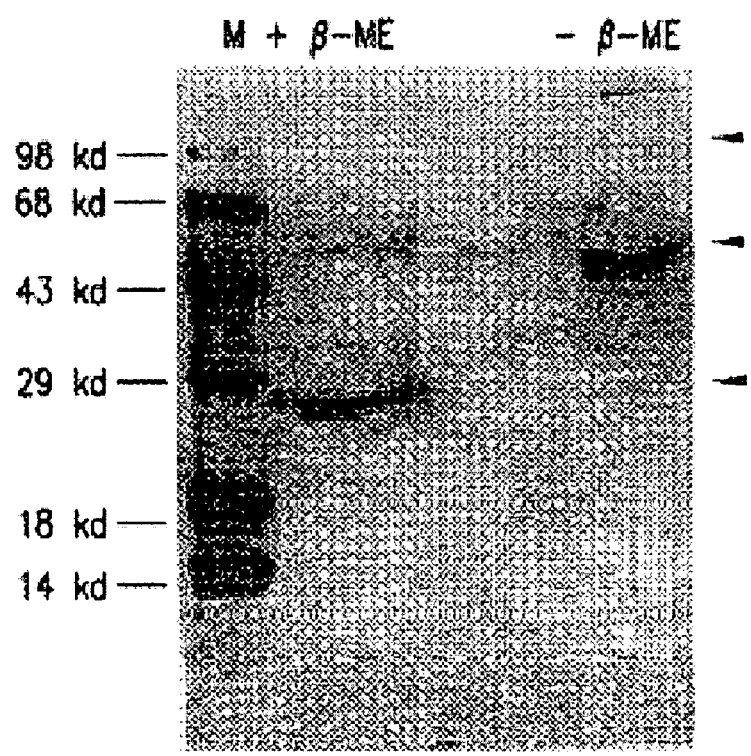
FIG. 10 depicts a photograph of an SDS-PAGE gel. VEGF2 was purified from the medium supernatant and analyzed by SDS-PAGE in the presence or absence of the reducing agent β-mercaptoethanol and stained by coomassie brilliant blue.
Figure 11:
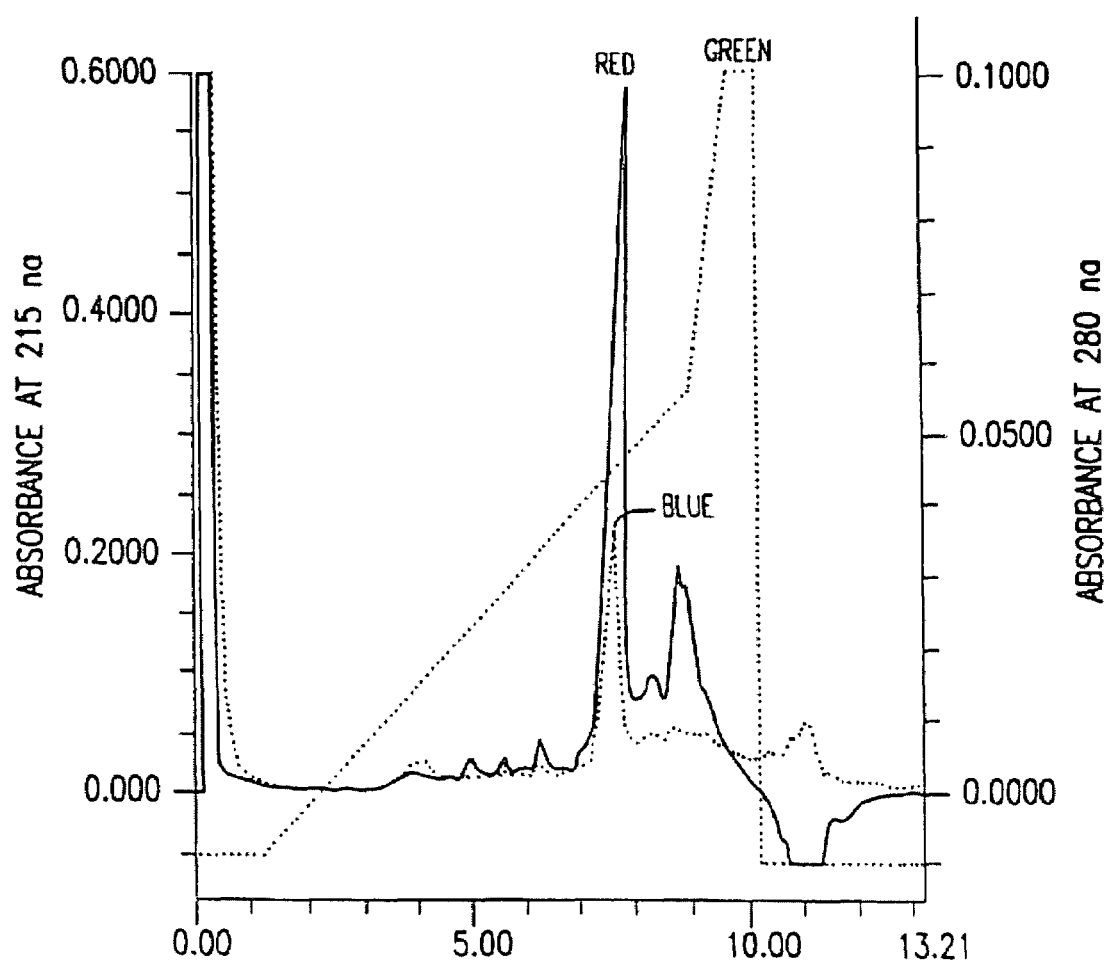
FIG. 11 depicts reverse phase HPLC analysis of purified VEGF2 using a RP-300 column (0.21×3 cm, Applied Biosystems, Inc.). The column was equilibrated with 0.1% trifluoroacetic acid (Solvent A) and the proteins eluted with a 7.5 min gradient from 0 to 60% Solvent B, composed of acetonitrile containing 0.07% TFA. The protein elution was monitored by absorbance at 215 nm ("red" line) and 280 nm ("blue" line). The percentage of Solvent B is shown by the "green" line.

The medium supernatant was also diluted 1:10 in 50 mM MES, pH 5.8 and applied to an SP-650M column (1.0×6.6 cm, Toyopearl) at a flow rate of 1 ml/min. Protein was eluted with step gradients at 200, 300 and 500 mM NaCl. The VEGF2 was obtained using the elution at 500 mM. The eluate was analyzed by SDS-PAGE in the presence or absence of reducing agent, β-mercaptoethanol and stained by Coommassie Brilliant Blue. See FIG. 10.

EXAMPLE 4

Expression of Recombinant VEGF2 in COS Cells

The expression of plasmid, VEGF2-HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, an SV40 intron and polyadenylation site. A DNA fragment encoding the entire VEGF2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (Wilson et al., *Cell* 37:767 (1984)). The infusion of HA tag to the target protein allows easy detection of the recombinant protein with an antibody that recognizes the HA epitope.

The plasmid construction strategy is described as follows:

The DNA sequence encoding VEGF2, ATCC No. 97149, was constructed by PCR using two primers: the 5' primer (CGC GGA TCC ATG ACT GTA CTC TAC CCA) (SEQ ID NO: 14) contains a BamH1 site followed by 18 nucleotides of VEGF2 coding sequence starting from the initiation codon; the 3' sequence (CGC TCT AGA TCA AGC GTA GTC TGG GAC GTC GTA TGG GTA CTC GAG GCT CAT TTG TGG TCT 3') (SEQ ID NO:15) contains complementary sequences to an XbaI site, HA tag, XhoI site, and the last 15 nucleotides of the VEGF2 coding sequence (not including the stop codon). Therefore, the PCR product contains a BamHI site, coding sequence followed by an XhoI restriction endonuclease site and HA tag fused in frame, a translation termination stop codon next to the HA tag, and an XbaI site. The PCR amplified DNA fragment and the vector, pcDNAI/Amp, were digested with BamH1 and XbaI restriction enzyme and ligated. The ligation mixture was transformed into *E. coli* strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant VEGF2, COS cells were transfected with the expression vector by DEAE-DEXTRAN method (J. Sambrook, E. Fritsch, T. Maniatis, *Molecular Cloning: A Laboratory Manual*, Cold Spring Laboratory Press, (1989)). The expression of the VEGF2-HA protein was detected by radiolabelling and immunoprecipitation method (E.

Harlow and D. Lane, *Antibodies: A Laboratory Manual*, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson et al., *Cell* 37:767 (1984)). Both cell lysate and culture media were precipitated with an HA specific monoclonal antibody. Proteins precipitated were analyzed on 15% SDS-PAGE gels.

EXAMPLE 5

The Effect of Partially Purified VEGF2 Protein on the Growth of Vascular Endothelial Cells On day 1, human umbilical vein endothelial cells (HUVEC) were seeded at 2–5×10⁴ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium was replaced with M199 containing 10% FBS, 8 units/ml heparin. VEGF2 protein of SEQ ID NO. 2 minus the initial 45 amino acid residues, (VEGF) and basic FGF (bFGF) were added, at the concentration shown. On days 4 and 6, the medium was replaced. On day 8, cell number was determined with a Coulter Counter (See FIG. 12).

EXAMPLE 6

The Effect of Purifed VEGF2 Protein on the Growth of Vascular Endothelial Cells On day 1, human umbilical vein endothelial cells (HUVEC) were seeded at 2–5×10⁴ cells/35 mm dish density in M199 medium containing 4% fetal bovine serum (FBS), 16 units/ml heparin, 50 units/ml endothelial cell growth supplements (ECGS, Biotechnique, Inc.). On day 2, the medium was replaced with M199 containing 10% FBS, 8 units/ml heparin. Purified VEGF2 protein of SEQ ID NO:2 minus initial 45 amino acid residues was added to the medium at this point. On days 4 and 6, the medium was replaced with fresh medium and supplements. On day 8, cell number was determined with a Coulter Counter (See FIG. 13).

EXAMPLE 7

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219–225 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively.

The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB 101, which are then plated onto agar-containing kanamycin for the purpose of confirming that the vector had the gene of interest properly inserted.

The amphotropic pA317 or GP+am 12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. A purified protein produced by the method comprising:
   (a) expressing a protein encoded by the cDNA contained in ATCC Deposit No. 97149 from a host cell; and
   (b) recovering said protein.

2. The purified protein of claim 1, wherein the protein is recovered from a natural source.

3. The purified protein of claim 1, wherein the protein is recovered from a recombinant host cell engineered to express the protein.

4. The purified protein of claim 1, wherein the protein is recovered from a mammalian cell.

5. The purified protein of claim 1, wherein the protein is recovered from a bacterial cell.

6. The purified protein of claim 1, wherein the protein is recovered from a baculovirus cell.

7. The purified protein of claim 1, wherein the protein is recovered from a yeast cell.

8. The purified protein of claim 1, wherein the protein is recovered by chromatography.

9. The purified protein of claim 1, wherein the protein is recovered by an antibody.

10. The purified protein of claim 1, wherein the protein is a homodimer.

11. The purified protein of claim 1, wherein the protein is fused to a heterologous polypeptide.

12. A composition comprising the purified protein of claim 1 and a pharmaceutically acceptable carrier.

13. A method of stimulating proliferation of endothelial cells in a patient comprising administering to the patient the purified protein of claim 1, wherein the patient has a wound, tissue, or bone damage.

14. A method of stimulating proliferation of endothelial cells in a patient comprising administering to the patient the purified protein of claim 1, wherein the patient has ischemia.

15. A method of stimulating proliferation of endothelial cells in a patient comprising administering to the patient the purified protein of claim 1, wherein the patient has had a myocardial infarction.

16. A method of stimulating proliferation of endothelial cells in a patient comprising administering to the patient the purified protein of claim 1, wherein the patient has coronary artery disease, peripheral vascular disease, or CNS vascular disease.

17. A method of stimulating angiogenesis in a patient comprising administering to the patient the purified protein of claim 1, wherein the patient has a wound, tissue, or bone damage.

18. A method of stimulating angiogenesis in a patient comprising administering to the patient the purified protein of claim 1, wherein the patient has ischemia.

19. A method of stimulating angiogenesis in a patient comprising administering to the patient the purified protein of claim 1, wherein the patient has had a myocardial infarction.

20. A method of stimulating angiogenesis in a patient comprising administering to the patient the purified protein of claim 1, wherein the patient has coronary artery disease, peripheral vascular disease, or CNS vascular disease.

21. A purified protein produced by the method comprising:
   (a) expressing a protein comprising amino acids 71 to 396 of SEQ ID NO:2 from a host cell; and
   (b) recovering said protein.

22. The purified protein of claim 21, wherein the protein is recovered from a natural source.

23. The purified protein of claim 21, wherein the protein is recovered from a recombinant host cell engineered to express the protein.

24. The purified protein of claim 21, wherein the protein is recovered from a mammalian cell.

25. The purified protein of claim 21, wherein the protein is recovered from a bacterial cell.

26. The purified protein of claim 21, wherein the protein is recovered from a baculovirus cell.

27. The purified protein of claim 21, wherein the protein is recovered from a yeast cell.

28. The purified protein of claim 21, wherein the protein is recovered by chromatography.

29. The purified protein of claim 21, wherein the protein is recovered by an antibody.

30. The purified protein of claim 21, wherein the protein is a homodimer.

31. The purified protein of claim 21, wherein the protein is fused to a heterologous polypeptide.

32. A composition comprising the purified protein of claim 21 and a pharmaceutically acceptable carrier.

33. A method of stimulating proliferation of endothelial cells in a patient comprising administering to the patient the purified protein of claim 21, wherein the patient has a wound, tissue, or bone damage.

34. A method of stimulating proliferation of endothelial cells in a patient comprising administering to the patient the purified protein of claim 21, wherein the patient has ischemia.

35. A method of stimulating proliferation of endothelial cells in a patient comprising administering to the patient the purified protein of claim 21, wherein the patient has had a myocardial infarction.

36. A method of stimulating proliferation of endothelial cells in a patient comprising administering to the patient the purified protein of claim 21, wherein the patient has coronary artery disease, peripheral vascular disease, or CNS vascular disease.

37. A method of stimulating angiogenesis in a patient comprising administering to the patient the purified protein of claim 21, wherein the patient has a wound, tissue, or bone damage.

38. A method of stimulating angiogenesis in a patient comprising administering to the patient the purified protein of claim 21, wherein the patient has ischemia.

39. A method of stimulating angiogenesis in a patient comprising administering to the patient the purified protein of claim 21, wherein the patient has had a myocardial infarction.

40. A method of stimulating angiogenesis in a patient comprising administering to the patient the purified protein of claim 21, wherein the patient has coronary artery disease, peripheral vascular disease, or CNS vascular disease.

41. A purified protein produced by the method comprising:
   (a) expressing a protein comprising amino acids 24 to 396 of SEQ ID NO:2 from a host cell; and
   (b) recovering said protein.

42. The purified protein of claim 41, wherein the protein is recovered from a natural source.

43. The purified protein of claim 41, wherein the protein is recovered from a recombinant host cell engineered to express the protein.

44. The purified protein of claim 41, wherein the protein is recovered from a mammalian cell.

45. The purified protein of claim 41, wherein the protein is recovered from a bacterial cell.

46. The purified protein of claim 41, wherein the protein is recovered from a baculovirus cell.

47. The purified protein of claim 41, wherein the protein is recovered from a yeast cell.

48. The purified protein of claim 41, wherein the protein is recovered by chromatography.

49. The purified protein of claim 41, wherein the protein is recovered by an antibody.

50. The purified protein of claim 41, wherein the protein is a homodimer.

51. The purified protein of claim 41, wherein the protein is fused to a heterologous polypeptide.

52. A composition comprising the purified protein of claim 41 and a pharmaceutically acceptable carrier.

53. A method of stimulating proliferation of endothelial cells in a patient comprising administering to the patient the purified protein of claim 41, wherein the patient has a wound, tissue, or bone damage.

54. A method of stimulating proliferation of endothelial cells in a patient comprising administering to the patient the purified protein of claim 41, wherein the patient has ischemia.

55. A method of stimulating proliferation of endothelial cells in a patient comprising administering to the patient the purified protein of claim 41, wherein the patient has had a myocardial infarction.

56. A method of stimulating proliferation of endothelial cells in a patient comprising administering to the patient the purified protein of claim 41, wherein the patient has coronary artery disease, peripheral vascular disease, or CNS vascular disease.

57. A method of stimulating angiogenesis in a patient comprising administering to the patient the purified protein of claim 41, wherein the patient has a wound, tissue, or bone damage.

58. A method of stimulating angiogenesis in a patient comprising administering to the patient the purified protein of claim 41, wherein the patient has ischemia.

59. A method of stimulating angiogenesis in a patient comprising administering to the patient the purified protein of claim 41, wherein the patient has had a myocardial infarction.

60. A method of stimulating angiogenesis in a patient comprising administering to the patient the purified protein of claim 41, wherein the patient has coronary artery disease, peripheral vascular disease, or CNS vascular disease.

61. A purified protein produced by the method comprising:
   (a) expressing a protein comprising amino acids 1 to 396 of SEQ ID NO:2 from a host cell; and
   (b) recovering said protein.

62. The purified protein of claim 61, wherein the protein is recovered from a natural source.

63. The purified protein of claim 61, wherein the protein is recovered from a recombinant host cell engineered to express the protein.

64. The purified protein of claim 61, wherein the protein is recovered from a mammalian cell.

65. The purified protein of claim 61, wherein the protein is recovered from a bacterial cell.

66. The purified protein of claim 61, wherein the protein is recovered from a baculovirus cell.

67. The purified protein of claim 61, wherein the protein is recovered from a yeast cell.

68. The purified protein of claim 61, wherein the protein is recovered by chromatography.

69. The purified protein of claim 61, wherein the protein is recovered by an antibody.

70. The purified protein of claim 61, wherein the protein is a homodimer.

71. The purified protein of claim 61, wherein the protein is fused to a heterologous polypeptide.

72. A composition comprising the purified protein of claim 61 and a pharmaceutically acceptable carrier.

73. A method of stimulating proliferation of endothelial cells in a patient comprising administering to the patient the purified protein of claim 61, wherein the patient has a wound, tissue, or bone damage.

74. A method of stimulating proliferation of endothelial cells in a patient comprising administering to the patient the purified protein of claim 61, wherein the patient has ischemia.

75. A method of stimulating proliferation of endothelial cells in a patient comprising administering to the patient the purified protein of claim 61, wherein the patient has had a myocardial infarction.

76. A method of stimulating proliferation of endothelial cells in a patient comprising administering to the patient the purified protein of claim 61, wherein the patient has coronary artery disease, peripheral vascular disease, or CNS vascular disease.

77. A method of stimulating angiogenesis in a patient comprising administering to the patient the purified protein of claim 61, wherein the patient has a wound, tissue, or bone damage.

78. A method of stimulating angiogenesis in a patient comprising administering to the patient the purified protein of claim 61, wherein the patient has ischemia.

79. A method of stimulating angiogenesis in a patient comprising administering to the patient the purified protein of claim 61, wherein the patient has had a myocardial infarction.

80. A method of stimulating angiogenesis in a patient comprising administering to the patient the purified protein of claim 61, wherein the patient has coronary artery disease, peripheral vascular disease, or CNS vascular disease.

81. A purified protein produced by the method comprising:
    (a) expressing a protein comprising amino acids −23 to 396 of SEQ ID NO:2 from a host cell; and
    (b) recovering said protein.

82. The purified protein of claim 81, wherein the protein is recovered from a natural source.

83. The purified protein of claim 81, wherein the protein is recovered from a recombinant host cell engineered to express the protein.

84. The purified protein of claim 81, wherein the protein is recovered from a mammalian cell.

85. The purified protein of claim 81, wherein the protein is recovered from a bacterial cell.

86. The purified protein of claim 81, wherein the protein is recovered from a baculovirus cell.

87. The purified protein of claim 81, wherein the protein is recovered from a yeast cell.

88. The purified protein of claim 81, wherein the protein is recovered by chromatography.

89. The purified protein of claim 81, wherein the protein is recovered by an antibody.

90. The purified protein of claim 81, wherein the protein is a homodimer.

91. The purified protein of claim 81, wherein the protein is fused to a heterologous polypeptide.

92. A composition comprising the purified protein of claim 81 and a pharmaceutically acceptable carrier.

93. A method of stimulating proliferation of endothelial cells in a patient comprising administering to the patient the purified protein of claim 81, wherein the patient has a wound, tissue, or bone damage.

94. A method of stimulating proliferation of endothelial cells in a patient comprising administering to the patient the purified protein of claim 81, wherein the patient has ischemia.

95. A method of stimulating proliferation of endothelial cells in a patient comprising administering to the patient the purified protein of claim 81, wherein the patient has had a myocardial infarction.

96. A method of stimulating proliferation of endothelial cells in a patient comprising administering to the patient the purified protein of claim 81, wherein the patient has coronary artery disease, peripheral vascular disease, or CNS vascular disease.

97. A method of stimulating angiogenesis in a patient comprising administering to the patient the purified protein of claim 81, wherein the patient has a wound, tissue, or bone damage.

98. A method of stimulating angiogenesis in a patient comprising administering to the patient the purified protein of claim 81, wherein the patient has ischemia.

99. A method of stimulating angiogenesis in a patient comprising administering to the patient the purified protein of claim 81, wherein the patient has had a myocardial infarction.

100. A method of stimulating angiogenesis in a patient comprising administering to the patient the purified protein of claim 81, wherein the patient has coronary artery disease, peripheral vascular disease, or CNS vascular disease.

101. A purified protein fragment produced by the method comprising:
    (a) expressing a protein fragment of SEQ ID NO:2 from a host cell, wherein said protein fragment comprises amino acids 108–188 of SEQ ID NO:2 and promotes angiogenesis; and
    (b) recovering said protein fragment.

102. The purified protein fragment of claim 101, wherein the protein fragment is recovered from a natural source.

103. The purified protein fragment of claim 101, wherein the protein fragment is recovered from a recombinant host cell engineered to express the protein fragment.

104. The purified protein fragment of claim 101, wherein the protein fragment is recovered from a mammalian cell.

105. The purified protein fragment of claim 101, wherein the protein fragment is recovered from a bacterial cell.

106. The purified protein fragment of claim 101, wherein the protein fragment is recovered from a baculovirus cell.

107. The purified protein fragment of claim 101, wherein the protein fragment is recovered from a yeast cell.

108. The purified protein fragment of claim 101, wherein the protein fragment is recovered by chromatography.

109. The purified protein fragment of claim 101, wherein the protein fragment is recovered by an antibody.

110. The purified protein fragment of claim 101, wherein the protein fragment is a homodimer.

111. The purified protein fragment of claim 101, wherein the protein fragment is fused to a heterologous polypeptide.

112. A composition comprising the purified protein fragment of claim 101 and a pharmaceutically acceptable carrier.

113. A method of stimulating proliferation of endothelial cells in a patient comprising administering to the patient the purified protein fragment of claim 101, wherein the patient has a wound, tissue, or bone damage.

114. A method of stimulating proliferation of endothelial cells in a patient comprising administering to the patient the purified protein fragment of claim 101, wherein the patient has ischemia.

115. A method of stimulating proliferation of endothelial cells in a patient comprising administering to the patient the purified protein fragment of claim 101, wherein the patient has had a myocardial infarction.

116. A method of stimulating proliferation of endothelial cells in a patient comprising administering to the patient the purified protein fragment of claim 101, wherein the patient has coronary artery disease, peripheral vascular disease, or CNS vascular disease.

117. A method of stimulating angiogenesis in a patient comprising administering to the patient the purified protein fragment of claim 101, wherein the patient has a wound, tissue, or bone damage.

118. A method of stimulating angiogenesis in a patient comprising administering to the patient the purified protein fragment of claim 101, wherein the patient has ischemia.

119. A method of stimulating angiogenesis in a patient comprising administering to the patient the purified protein fragment of claim 101, wherein the patient has had a myocardial infarction.

120. A method of stimulating angiogenesis in a patient comprising administering to the patient the purified protein fragment of claim 101, wherein the patient has coronary artery disease, peripheral vascular disease, or CNS vascular disease.

121. A purified protein fragment produced by the method comprising:
 (a) expressing a protein fragment of the protein encoded by the cDNA contained in ATCC Deposit No. 97149 from a host cell, wherein said protein fragment comprises amino acids 108–188 of SEQ ID NO:2 and promotes angiogenesis; and
 (b) recovering said protein fragment.

122. The purified protein fragment of claim 121, wherein the protein fragment is recovered from a natural source.

123. The purified protein fragment of claim 121, wherein the protein fragment is recovered from a recombinant host cell engineered to express the protein fragment.

124. The purified protein fragment of claim 121, wherein the protein fragment is recovered from a mammalian cell.

125. The purified protein fragment of claim 121, wherein the protein fragment is recovered from a bacterial cell.

126. The purified protein fragment of claim 121, wherein the protein fragment is recovered from a baculovirus cell.

127. The purified protein fragment of claim 121, wherein the protein fragment is recovered from a yeast cell.

128. The purified protein fragment of claim 121, wherein the protein fragment is recovered by chromatography.

129. The purified protein fragment of claim 121, wherein the protein fragment is recovered by an antibody.

130. The purified protein fragment of claim 121, wherein the protein fragment is a homodimer.

131. The purified protein fragment of claim 121, wherein the protein fragment is fused to a heterologous polypeptide.

132. A composition comprising the purified protein fragment of claim 121 and a pharmaceutically acceptable carrier.

133. A method of stimulating proliferation of endothelial cells in a patient comprising administering to the patient the purified protein fragment of claim 121, wherein the patient has a wound, tissue, or bone damage.

134. A method of stimulating proliferation of endothelial cells in a patient comprising administering to the patient the purified protein fragment of claim 121, wherein the patient has ischemia.

135. A method of stimulating proliferation of endothelial cells in a patient comprising administering to the patient the purified protein fragment of claim 121, wherein the patient has had a myocardial infarction.

136. A method of stimulating proliferation of endothelial cells in a patient comprising administering to the patient the purified protein fragment of claim 121, wherein the patient has coronary artery disease, peripheral vascular disease, or CNS vascular disease.

137. A method of stimulating angiogenesis in a patient comprising administering to the patient the purified protein fragment of claim 121, wherein the patient has a wound, tissue, or bone damage.

138. A method of stimulating angiogenesis in a patient comprising administering to the patient the purified protein fragment of claim 121, wherein the patient has ischemia.

139. A method of stimulating angiogenesis in a patient comprising administering to the patient the purified protein fragment of claim 121, wherein the patient has had a myocardial infarction.

140. A method of stimulating angiogenesis in a patient comprising administering to the patient the purified protein fragment of claim 121, wherein the patient has coronary artery disease, peripheral vascular disease, or CNS vascular disease.

141. A purified protein fragment produced by the method comprising:
 (a) expressing a protein fragment of SEQ ID NO:2 from a host cell, wherein said protein fragment comprises amino acids 108–188 of SEQ ID NO:2 and proliferates endothelial cells; and
 (b) recovering said protein fragment.

142. The purified protein fragment of claim 141, wherein the protein fragment is recovered from a natural source.

143. The purified protein fragment of claim 141, wherein the protein fragment is recovered from a recombinant host cell engineered to express the protein fragment.

144. The purified protein fragment of claim 141, wherein the protein fragment is recovered from a mammalian cell.

145. The purified protein fragment of claim 141, wherein the protein fragment is recovered from a bacterial cell.

146. The purified protein fragment of claim 141, wherein the protein fragment is recovered from a baculovirus cell.

147. The purified protein fragment of claim 141, wherein the protein fragment is recovered from a yeast cell.

148. The purified protein fragment of claim 141, wherein the protein fragment is recovered by chromatography.

149. The purified protein fragment of claim 141, wherein the protein fragment is recovered by an antibody.

150. The purified protein fragment of claim 141, wherein the protein fragment is a homodimer.

151. The purified protein fragment of claim 141, wherein the protein fragment is fused to a heterologous polypeptide.

152. A composition comprising the purified protein fragment of claim 141 and a pharmaceutically acceptable carrier.

153. A method of stimulating proliferation of endothelial cells in a patient comprising administering to the patient the purified protein fragment of claim 141, wherein the patient has a wound, tissue, or bone damage.

154. A method of stimulating proliferation of endothelial cells in a patient comprising administering to the patient the purified protein fragment of claim 141, wherein the patient has ischemia.

155. A method of stimulating proliferation of endothelial cells in a patient comprising administering to the patient the purified protein fragment of claim 141, wherein the patient has had a myocardial infarction.

156. A method of stimulating proliferation of endothelial cells in a patient comprising administering to the patient the purified protein fragment of claim 141, wherein the patient has coronary artery disease, peripheral vascular disease, or CNS vascular disease.

157. A method of stimulating angiogenesis in a patient comprising administering to the patient the purified protein fragment of claim 141, wherein the patient has a wound, tissue, or bone damage.

158. A method of stimulating angiogenesis in a patient comprising administering to the patient the purified protein fragment of claim 141, wherein the patient has ischemia.

159. A method of stimulating angiogenesis in a patient comprising administering to the patient the purified protein fragment of claim 141, wherein the patient has had a myocardial infarction.

160. A method of stimulating angiogenesis in a patient comprising administering to the patient the purified protein fragment of claim 141, wherein the patient has coronary artery disease, peripheral vascular disease, or CNS vascular disease.

161. A purified protein fragment produced by the method comprising:
 (a) expressing a protein fragment of the protein encoded by the cDNA contained in ATCC Deposit No. 97149 from a host cell, wherein said protein fragment comprises amino acids 108–188 of SEQ ID NO:2 and proliferates endothelial cells; and
 (b) recovering said protein fragment.

162. The purified protein fragment of claim 161, wherein the protein fragment is recovered from a natural source.

163. The purified protein fragment of claim 161, wherein the protein fragment is recovered from a recombinant host cell engineered to express the protein fragment.

164. The purified protein fragment of claim 161, wherein the protein fragment is recovered from a mammalian cell.

165. The purified protein fragment of claim 161, wherein the protein fragment is recovered from a bacterial cell.

166. The purified protein fragment of claim 161, wherein the protein fragment is recovered from a baculovirus cell.

167. The purified protein fragment of claim 161, wherein the protein fragment is recovered from a yeast cell.

168. The purified protein fragment of claim 161, wherein the protein fragment is recovered by chromatography.

169. The purified protein fragment of claim 161, wherein the protein fragment is recovered by an antibody.

170. The purified protein fragment of claim 161, wherein the protein fragment is a homodimer.

171. The purified protein fragment of claim 161, wherein the protein fragment is fused to a heterologous polypeptide.

172. A composition comprising the purified protein fragment of claim 161 and a pharmaceutically acceptable carrier.

173. A method of stimulating proliferation of endothelial cells in a patient comprising administering to the patient the purified protein fragment of claim 161, wherein the patient has a wound, tissue, or bone damage.

174. A method of stimulating proliferation of endothelial cells in a patient comprising administering to the patient the purified protein fragment of claim 161, wherein the patient has ischemia.

175. A method of stimulating proliferation of endothelial cells in a patient comprising administering to the patient the purified protein fragment of claim 161, wherein the patient has had a myocardial infarction.

176. A method of stimulating proliferation of endothelial cells in a patient comprising administering to the patient the purified protein fragment of claim 161, wherein the patient has coronary artery disease, peripheral vascular disease, or CNS vascular disease.

177. A method of stimulating angiogenesis in a patient comprising administering to the patient the purified protein fragment of claim 161, wherein the patient has a wound, tissue, or bone damage.

178. A method of stimulating angiogenesis in a patient comprising administering to the patient the purified protein fragment of claim 161, wherein the patient has ischemia.

179. A method of stimulating angiogenesis in a patient comprising administering to the patient the purified protein fragment of claim 161, wherein the patient has had a myocardial infarction.

180. A method of stimulating angiogenesis in a patient comprising administering to the patient the purified protein fragment of claim 161, wherein the patient has coronary artery disease, peripheral vascular disease, or CNS vascular disease.

181. A purified protein produced by the method comprising:
 (a) expressing a protein encoded by the cDNA contained in ATCC Deposit Nos. 75698 from a host cell; and
 (b) recovering said protein.

182. The purified protein of claim 181, wherein the protein is recovered from a natural source.

183. The purified protein of claim 181, wherein the protein is recovered from a recombinant host cell engineered to express the protein.

184. The purified protein of claim 181, wherein the protein is recovered from a mammalian cell.

185. The purified protein of claim 181, wherein the protein is recovered from a bacterial cell.

186. The purified protein of claim 181, wherein the protein is recovered from a baculovirus cell.

187. The purified protein of claim 181, wherein the protein is recovered from a yeast cell.

188. The purified protein of claim 181, wherein the protein is recovered by chromatography.

189. The purified protein of claim 181, wherein the protein is recovered by an antibody.

190. The purified protein of claim 181, wherein the protein is a homodimer.

191. The purified protein of claim 181, wherein the protein is fused to a heterologous polypeptide.

192. A composition comprising the purified protein of claim 181 and a pharmaceutically acceptable carrier.

193. A method of stimulating proliferation of endothelial cells in a patient comprising administering to the patient the purified protein of claim 181, wherein the patient has a wound, tissue, or bone damage.

194. A method of stimulating proliferation of endothelial cells in a patient comprising administering to the patient the purified protein of claim 181, wherein the patient has ischemia.

195. A method of stimulating proliferation of endothelial cells in a patient comprising administering to the patient the purified protein of claim 181, wherein the patient has had a myocardial infarction.

196. A method of stimulating proliferation of endothelial cells in a patient comprising administering to the patient the purified protein of claim 181, wherein the patient has coronary artery disease, peripheral vascular disease, or CNS vascular disease.

197. A method of stimulating angiogenesis in a patient comprising administering to the patient the purified protein of claim 181, wherein the patient has a wound, tissue, or bone damage.

198. A method of stimulating angiogenesis in a patient comprising administering to the patient the purified protein of claim 181, wherein the patient has ischemia.

199. A method of stimulating angiogenesis in a patient comprising administering to the patient the purified protein of claim 181, wherein the patient has had a myocardial infarction.

200. A method of stimulating angiogenesis in a patient comprising administering to the patient the purified protein of claim 181, wherein the patient has coronary artery disease, peripheral vascular disease, or CNS vascular disease.

201. A purified protein fragment produced by the method comprising:
(a) expressing a protein fragment of the protein encoded by the cDNA contained in ATCC Deposit No. 75698 from a host cell, wherein said protein fragment comprises amino acids 38–118 of SEQ ID NO:4 and promotes angiogenesis; and
(b) recovering said protein fragment.

202. The purified protein fragment of claim 201, wherein the protein fragment is recovered from a natural source.

203. The purified protein fragment of claim 201, wherein the protein fragment is recovered from a recombinant host cell engineered to express the protein fragment.

204. The purified protein fragment of claim 201, wherein the protein fragment is recovered from a mammalian cell.

205. The purified protein fragment of claim 201, wherein the protein fragment is recovered from a bacterial cell.

206. The purified protein fragment of claim 201, wherein the protein fragment is recovered from a baculovirus cell.

207. The purified protein fragment of claim 201, wherein the protein fragment is recovered from a yeast cell.

208. The purified protein fragment of claim 201, wherein the protein fragment is recovered by chromatography.

209. The purified protein fragment of claim 201, wherein the protein fragment is recovered by an antibody.

210. The purified protein fragment of claim 201, wherein the protein fragment is a homodimer.

211. The purified protein fragment of claim 201, wherein the protein fragment is fused to a heterologous polypeptide.

212. A composition comprising the purified protein fragment of claim 201 and a pharmaceutically acceptable carrier.

213. A method of stimulating proliferation of endothelial cells in a patient comprising administering to the patient the purified protein fragment of claim 201, wherein the patient has a wound, tissue, or bone damage.

214. A method of stimulating proliferation of endothelial cells in a patient comprising administering to the patient the purified protein fragment of claim 201, wherein the patient has ischemia.

215. A method of stimulating proliferation of endothelial cells in a patient comprising administering to the patient the purified protein fragment of claim 201, wherein the patient has had a myocardial infarction.

216. A method of stimulating proliferation of endothelial cells in a patient comprising administering to the patient the purified protein fragment of claim 201, wherein the patient has coronary artery disease, peripheral vascular disease, or CNS vascular disease.

217. A method of stimulating angiogenesis in a patient comprising administering to the patient the purified protein fragment of claim 201, wherein the patient has a wound, tissue, or bone damage.

218. A method of stimulating angiogenesis in a patient comprising administering to the patient the purified protein fragment of claim 201, wherein the patient has ischemia.

219. A method of stimulating angiogenesis in a patient comprising administering to the patient the purified protein fragment of claim 201, wherein the patient has had a myocardial infarction.

220. A method of stimulating angiogenesis in a patient comprising administering to the patient the purified protein fragment of claim 201, wherein the patient has coronary artery disease, peripheral vascular disease, or CNS vascular disease.

221. A purified protein fragment produced by the method comprising:
(a) expressing a protein fragment of the protein encoded by the cDNA contained in ATCC Deposit No. 75698 from a host cell, wherein said protein fragment comprises amino acids 38–118 of SEQ ID NO:4 and proliferates endothelial cells; and
(b) recovering said protein fragment.

222. The purified protein fragment of claim 221, wherein the protein fragment is recovered from a natural source.

223. The purified protein fragment of claim 221, wherein the protein fragment is recovered from a recombinant host cell engineered to express the protein fragment.

224. The purified protein fragment of claim 221, wherein the protein fragment is recovered from a mammalian cell.

225. The purified protein fragment of claim 221, wherein the protein fragment is recovered from a bacterial cell.

226. The purified protein fragment of claim 221, wherein the protein fragment is recovered from a baculovirus cell.

227. The purified protein fragment of claim 221, wherein the protein fragment is recovered from a yeast cell.

228. The purified protein fragment of claim 221, wherein the protein fragment is recovered by chromatography.

229. The purified protein fragment of claim 221, wherein the protein fragment is recovered by an antibody.

230. The purified protein fragment of claim 221, wherein the protein fragment is a homodimer.

231. The purified protein fragment of claim 221, wherein the protein fragment is fused to a heterologous polypeptide.

232. A composition comprising the purified protein fragment of claim 221 and a pharmaceutically acceptable carrier.

233. A method of stimulating proliferation of endothelial cells in a patient comprising administering to the patient the purified protein fragment of claim 221, wherein the patient has a wound, tissue, or bone damage.

234. A method of stimulating proliferation of endothelial cells in a patient comprising administering to the patient the purified protein fragment of claim 221, wherein the patient has ischemia.

235. A method of stimulating proliferation of endothelial cells in a patient comprising administering to the patient the purified protein fragment of claim 221, wherein the patient has had a myocardial infarction.

236. A method of stimulating proliferation of endothelial cells in a patient comprising administering to the patient the purified protein fragment of claim 221, wherein the patient has coronary artery disease, peripheral vascular disease, or CNS vascular disease.

237. A method of stimulating angiogenesis in a patient comprising administering to the patient the purified protein fragment of claim 221, wherein the patient has a wound, tissue, or bone damage.

238. A method of stimulating angiogenesis in a patient comprising administering to the patient the purified protein fragment of claim 221, wherein the patient has ischemia.

239. A method of stimulating angiogenesis in a patient comprising administering to the patient the purified protein fragment of claim 221, wherein the patient has had a myocardial infarction.

240. A method of stimulating angiogenesis in a patient comprising administering to the patient the purified protein fragment of claim 221, wherein the patient has coronary artery disease, peripheral vascular disease, or CNS vascular disease.

* * * * *

UNITED STATES PATENT AND TRADEMARK OFFICE
CERTIFICATE OF CORRECTION

PATENT NO. : 7,153,827 B1
APPLICATION NO. : 09/219442
DATED : December 26, 2006
INVENTOR(S) : Hu et al.

It is certified that error appears in the above-identified patent and that said Letters Patent is hereby corrected as shown below:

On the Title page, under the PTA Notice, above Section (21), please insert:

--This patent is subject to a terminal disclaimer.--

Signed and Sealed this

First Day of May, 2007

JON W. DUDAS
*Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1674 base pairs (B) TYPE: nucleic acid
            (C) STRANDEDNESS: double
            (D) TOPOLOGY: linear (ii) MOLECULE TYPE: cDNA (ix) FEATURE:
            (A) NAME/KEY: sig_peptide
            (B) LOCATION: 12..80

(ix) FEATURE:
            (A) NAME/KEY: mat_peptide
            (B) LOCATION: 81..1268

(ix) FEATURE:
            (A) NAME/KEY: CDS
            (B) LOCATION: 12..1268

(xi) SEQUENCE DESCRIPTION: SEQ ID NO:1:

```
GTCCTTCCAC C ATG CAC TCG CTG GGC TTC TTC TCT GTG GCG TGT TCT CTG      50
             Met His Ser Leu Gly Phe Phe Ser Val Ala Cys Ser Leu
             -23         -20                 -15

CTC GCC GCT GCG CTG CTC CCG GGT CCT CGC GAG GCG CCC GCC GCC GCC       98
Leu Ala Ala Ala Leu Leu Pro Gly Pro Arg Glu Ala Pro Ala Ala Ala
-10             -5                   1               5

GCC GCC TTC GAG TCC GGA CTC GAC CTC TCG GAC GCG GAG CCC GAC GCG      146
Ala Ala Phe Glu Ser Gly Leu Asp Leu Ser Asp Ala Glu Pro Asp Ala
            10                  15                  20

GGC GAG GCC ACG GCT TAT GCA AGC AAA GAT CTG GAG GAG CAG TTA CGG      194
Gly Glu Ala Thr Ala Tyr Ala Ser Lys Asp Leu Glu Glu Gln Leu Arg
            25                  30                  35

TCT GTG TCC AGT GTA GAT GAA CTC ATG ACT GTA CTC TAC CCA GAA TAT      242
Ser Val Ser Ser Val Asp Glu Leu Met Thr Val Leu Tyr Pro Glu Tyr
        40                  45                  50

TGG AAA ATG TAC AAG TGT CAG CTA AGG AAA GGA GGC TGG CAA CAT AAC      290
Trp Lys Met Tyr Lys Cys Gln Leu Arg Lys Gly Gly Trp Gln His Asn
55                  60                  65                  70

AGA GAA CAG GCC AAC CTC AAC TCA AGG ACA GAA GAG ACT ATA AAA TTT      338
Arg Glu Gln Ala Asn Leu Asn Ser Arg Thr Glu Glu Thr Ile Lys Phe
                75                  80                  85

GCT GCA GCA CAT TAT AAT ACA GAG ATC TTG AAA AGT ATT GAT AAT GAG      386
Ala Ala Ala His Tyr Asn Thr Glu Ile Leu Lys Ser Ile Asp Asn Glu
            90                  95                  100

TGG AGA AAG ACT CAA TGC ATG CCA CGG GAG GTG TGT ATA GAT GTG GGG      434
Trp Arg Lys Thr Gln Cys Met Pro Arg Glu Val Cys Ile Asp Val Gly
        105                 110                 115

AAG GAG TTT GGA GTC GCG ACA AAC ACC TTC TTT AAA CCT CCA TGT GTG      482
Lys Glu Phe Gly Val Ala Thr Asn Thr Phe Phe Lys Pro Pro Cys Val
    120                 125                 130

TCC GTC TAC AGA TGT GGG GGT TGC TGC AAT AGT GAG GGG CTG CAG TGC      530
Ser Val Tyr Arg Cys Gly Gly Cys Cys Asn Ser Glu Gly Leu Gln Cys
135                 140                 145                 150

ATG AAC ACC AGC ACG AGC TAC CTC AGC AAG ACG TTA TTT GAA ATT ACA      578
Met Asn Thr Ser Thr Ser Tyr Leu Ser Lys Thr Leu Phe Glu Ile Thr
                155                 160                 165

GTG CCT CTC TCT CAA GGC CCC AAA CCA GTA ACA ATC AGT TTT GCC AAT      626
Val Pro Leu Ser Gln Gly Pro Lys Pro Val Thr Ile Ser Phe Ala Asn
            170                 175                 180

CAC ACT TCC TGC CGA TGC ATG TCT AAA CTG GAT GTT TAC AGA CAA GTT      674
His Thr Ser Cys Arg Cys Met Ser Lys Leu Asp Val Tyr Arg Gln Val
        185                 190                 195

CAT TCC ATT ATT AGA CGT TCC CTG CCA GCA ACA CTA CCA CAG TGT CAG      722
His Ser Ile Ile Arg Arg Ser Leu Pro Ala Thr Leu Pro Gln Cys Gln
    200                 205                 210
```

```
GCA GCG AAC AAG ACC TGC CCC ACC AAT TAC ATG TGG AAT AAT CAC ATC              770
Ala Ala Asn Lys Thr Cys Pro Thr Asn Tyr Met Trp Asn Asn His Ile
215                 220                 225                 230

TGC AGA TGC CTG GCT CAG GAA GAT TTT ATG TTT TCC TCG GAT GCT GGA              818
Cys Arg Cys Leu Ala Gln Glu Asp Phe Met Phe Ser Ser Asp Ala Gly
                235                 240                 245

GAT GAC TCA ACA GAT GGA TTC CAT GAC ATC TGT GGA CCA AAC AAG GAG              866
Asp Asp Ser Thr Asp Gly Phe His Asp Ile Cys Gly Pro Asn Lys Glu
            250                 255                 260

CTG GAT GAA GAG ACC TGT CAG TGT GTC TGC AGA GCG GGG CTT CGG CCT              914
Leu Asp Glu Glu Thr Cys Gln Cys Val Cys Arg Ala Gly Leu Arg Pro
        265                 270                 275

GCC AGC TGT GGA CCC CAC AAA GAA CTA GAC AGA AAC TCA TGC CAG TGT              962
Ala Ser Cys Gly Pro His Lys Glu Leu Asp Arg Asn Ser Cys Gln Cys
    280                 285                 290

GTC TGT AAA AAC AAA CTC TTC CCC AGC CAA TGT GGG GCC AAC CGA GAA             1010
Val Cys Lys Asn Lys Leu Phe Pro Ser Gln Cys Gly Ala Asn Arg Glu
295                 300                 305                 310

TTT GAT GAA AAC ACA TGC CAG TGT GTA TGT AAA AGA ACC TGC CCC AGA             1058
Phe Asp Glu Asn Thr Cys Gln Cys Val Cys Lys Arg Thr Cys Pro Arg
                315                 320                 325

AAT CAA CCC CTA AAT CCT GGA AAA TGT GCC TGT GAA TGT ACA GAA AGT             1106
Asn Gln Pro Leu Asn Pro Gly Lys Cys Ala Cys Glu Cys Thr Glu Ser
            330                 335                 340

CCA CAG AAA TGC TTG TTA AAA GGA AAG AAG TTC CAC CAC CAA ACA TGC             1154
Pro Gln Lys Cys Leu Leu Lys Gly Lys Lys Phe His His Gln Thr Cys
        345                 350                 355

AGC TGT TAC AGA CGG CCA TGT ACG AAC CGC CAG AAG GCT TGT GAG CCA             1202
Ser Cys Tyr Arg Arg Pro Cys Thr Asn Arg Gln Lys Ala Cys Glu Pro
    360                 365                 370

GGA TTT TCA TAT AGT GAA GAA GTG TGT CGT TGT GTC CCT TCA TAT TGG             1250
Gly Phe Ser Tyr Ser Glu Glu Val Cys Arg Cys Val Pro Ser Tyr Trp
375                 380                 385                 390

CAA AGA CCA CAA ATG AGC TAAGATTGTA CTGTTTTCCA GTTCATCGAT                    1298
Gln Arg Pro Gln Met Ser
                395

TTTCTATTAT GGAAAACTGT GTTGCCACAG TAGAACTGTC TGTGAACAGA GAGACCCTTG           1358

TGGGTCCATG CTAACAAAGA CAAAAGTCTG TCTTTCCTGA ACCATGTGGA TAACTTTACA           1418

GAAATGGACT GGAGCTCATC TGCAAAAGGC CTCTTGTAAA GACTGGTTTT CTGCCAATGA           1478

CCAAACAGCC AAGATTTTCC TCTTGTGATT TCTTTAAAAG AATGACTATA TAATTTATTT           1538

CCACTAAAAA TATTGTTTCT GCATTCATTT TTATAGCAAC AACAATTGGT AAAACTCACT           1598

GTGATCAATA TTTTTATATC ATGCAAAATA TGTTTAAAAT AAAATGAAAA TTGTATTTAT           1658

AAAAAAAAAA AAAAAA                                                           1674

(2) INFORMATION FOR SEQ ID NO:2:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:2:

Met His Ser Leu Gly Phe Phe Ser Val Ala Cys Ser Leu Leu Ala Ala
-23             -20                 -15                 -10

Ala Leu Leu Pro Gly Pro Arg Glu Ala Pro Ala Ala Ala Ala Ala Phe
```

```
        -5                    1                    5
Glu  Ser  Gly  Leu  Asp  Leu  Ser  Asp  Ala  Glu  Pro  Asp  Ala  Gly  Glu  Ala
 10                 15                  20                            25

Thr  Ala  Tyr  Ala  Ser  Lys  Asp  Leu  Glu  Glu  Gln  Leu  Arg  Ser  Val  Ser
                30                  35                            40

Ser  Val  Asp  Glu  Leu  Met  Thr  Val  Leu  Tyr  Pro  Glu  Tyr  Trp  Lys  Met
           45                       50                       55

Tyr  Lys  Cys  Gln  Leu  Arg  Lys  Gly  Gly  Trp  Gln  His  Asn  Arg  Glu  Gln
      60                       65                       70

Ala  Asn  Leu  Asn  Ser  Arg  Thr  Glu  Glu  Thr  Ile  Lys  Phe  Ala  Ala  Ala
 75                      80                       85

His  Tyr  Asn  Thr  Glu  Ile  Leu  Lys  Ser  Ile  Asp  Asn  Glu  Trp  Arg  Lys
 90                 95                      100                           105

Thr  Gln  Cys  Met  Pro  Arg  Glu  Val  Cys  Ile  Asp  Val  Gly  Lys  Glu  Phe
                110                      115                      120

Gly  Val  Ala  Thr  Asn  Thr  Phe  Phe  Lys  Pro  Pro  Cys  Val  Ser  Val  Tyr
                125                      130                      135

Arg  Cys  Gly  Cys  Cys  Asn  Ser  Glu  Gly  Leu  Gln  Cys  Met  Asn  Thr
           140                 145                      150

Ser  Thr  Ser  Tyr  Leu  Ser  Lys  Thr  Leu  Phe  Glu  Ile  Thr  Val  Pro  Leu
155                      160                      165

Ser  Gln  Gly  Pro  Lys  Pro  Val  Thr  Ile  Ser  Phe  Ala  Asn  His  Thr  Ser
170                      175                      180                      185

Cys  Arg  Cys  Met  Ser  Lys  Leu  Asp  Val  Tyr  Arg  Gln  Val  His  Ser  Ile
                190                      195                      200

Ile  Arg  Arg  Ser  Leu  Pro  Ala  Thr  Leu  Pro  Gln  Cys  Gln  Ala  Ala  Asn
                205                      210                      215

Lys  Thr  Cys  Pro  Thr  Asn  Tyr  Met  Trp  Asn  Asn  His  Ile  Cys  Arg  Cys
                220                      225                      230

Leu  Ala  Gln  Glu  Asp  Phe  Met  Phe  Ser  Ser  Asp  Ala  Gly  Asp  Asp  Ser
           235                      240                      245

Thr  Asp  Gly  Phe  His  Asp  Ile  Cys  Gly  Pro  Asn  Lys  Glu  Leu  Asp  Glu
250                      255                      260                      265

Glu  Thr  Cys  Gln  Cys  Val  Cys  Arg  Ala  Gly  Leu  Arg  Pro  Ala  Ser  Cys
                270                      275                      280

Gly  Pro  His  Lys  Glu  Leu  Asp  Arg  Asn  Ser  Cys  Gln  Cys  Val  Cys  Lys
                285                      290                      295

Asn  Lys  Leu  Phe  Pro  Ser  Gln  Cys  Gly  Ala  Asn  Arg  Glu  Phe  Asp  Glu
                300                      305                      310

Asn  Thr  Cys  Gln  Cys  Val  Cys  Lys  Arg  Thr  Cys  Pro  Arg  Asn  Gln  Pro
315                      320                      325

Leu  Asn  Pro  Gly  Lys  Cys  Ala  Cys  Glu  Cys  Thr  Glu  Ser  Pro  Gln  Lys
330                      335                      340                      345

Cys  Leu  Leu  Lys  Gly  Lys  Lys  Phe  His  His  Gln  Thr  Cys  Ser  Cys  Tyr
                350                      355                      360

Arg  Arg  Pro  Cys  Thr  Asn  Arg  Gln  Lys  Ala  Cys  Glu  Pro  Gly  Phe  Ser
                365                      370                      375

Tyr  Ser  Glu  Glu  Val  Cys  Arg  Cys  Val  Pro  Ser  Tyr  Trp  Gln  Arg  Pro
           380                      385                      390

Gln  Met  Ser
      395
```

(2) INFORMATION FOR SEQ ID NO:3:

```
    (i) SEQUENCE CHARACTERISTICS:
        (A) LENGTH: 1526 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig_peptide
        (B) LOCATION: 71..142

(ix) FEATURE:
        (A) NAME/KEY: mat_peptide
        (B) LOCATION: 143..1120

(ix) FEATURE:
        (A) NAME/KEY: CDS
        (B) LOCATION: 71..1120

(xi) SEQUENCE DESCRIPTION: SEQ ID NO:3:
```

| | | | | | |
|---|---|---|---|---|---|
| CGAGGCCACG | GCTTATGCAA | GCAAAGATCT | GGAGGAGCAG | TTACGGTCTG | TGTCCAGTGT | 60 |

```
AGATGAACTC ATG ACT GTA CTC TAC CCA GAA TAT TGG AAA ATG TAC AAG         109
           Met Thr Val Leu Tyr Pro Glu Tyr Trp Lys Met Tyr Lys
           -24             -20                 -15

TGT CAG CTA AGG AAA GGA GGC TGG CAA CAT AAC AGA GAA CAG GCC AAC         157
Cys Gln Leu Arg Lys Gly Gly Trp Gln His Asn Arg Glu Gln Ala Asn
        -10              -5                  1                   5

CTC AAC TCA AGG ACA GAA GAG ACT ATA AAA TTT GCT GCA GCA CAT TAT         205
Leu Asn Ser Arg Thr Glu Glu Thr Ile Lys Phe Ala Ala Ala His Tyr
                10                  15                  20

AAT ACA GAG ATC TTG AAA AGT ATT GAT AAT GAG TGG AGA AAG ACT CAA         253
Asn Thr Glu Ile Leu Lys Ser Ile Asp Asn Glu Trp Arg Lys Thr Gln
            25                  30                  35

TGC ATG CCA CGG GAG GTG TGT ATA GAT GTG GGG AAG GAG TTT GGA GTC         301
Cys Met Pro Arg Glu Val Cys Ile Asp Val Gly Lys Glu Phe Gly Val
        40                  45                  50

GCG ACA AAC ACC TTC TTT AAA CCT CCA TGT GTG TCC GTC TAC AGA TGT         349
Ala Thr Asn Thr Phe Phe Lys Pro Pro Cys Val Ser Val Tyr Arg Cys
    55                  60                  65

GGG GGT TGC TGC AAT AGT GAG GGG CTG CAG TGC ATG AAC ACC AGC ACG         397
Gly Gly Cys Cys Asn Ser Glu Gly Leu Gln Cys Met Asn Thr Ser Thr
70                  75                  80                  85

AGC TAC CTC AGC AAG ACG TTA TTT GAA ATT ACA GTG CCT CTC TCT CAA         445
Ser Tyr Leu Ser Lys Thr Leu Phe Glu Ile Thr Val Pro Leu Ser Gln
                90                  95                  100

GGC CCC AAA CCA GTA ACA ATC AGT TTT GCC AAT CAC ACT TCC TGC CGA         493
Gly Pro Lys Pro Val Thr Ile Ser Phe Ala Asn His Thr Ser Cys Arg
            105                 110                 115

TGC ATG TCT AAA CTG GAT GTT TAC AGA CAA GTT CAT TCC ATT ATT AGA         541
Cys Met Ser Lys Leu Asp Val Tyr Arg Gln Val His Ser Ile Ile Arg
        120                 125                 130

CGT TCC CTG CCA GCA ACA CTA CCA CAG TGT CAG GCA GCG AAC AAG ACC         589
Arg Ser Leu Pro Ala Thr Leu Pro Gln Cys Gln Ala Ala Asn Lys Thr
    135                 140                 145

TGC CCC ACC AAT TAC ATG TGG AAT AAT CAC ATC TGC AGA TGC CTG GCT         637
Cys Pro Thr Asn Tyr Met Trp Asn Asn His Ile Cys Arg Cys Leu Ala
150                 155                 160                 165

CAG GAA GAT TTT ATG TTT TCC TCG GAT GCT GGA GAT GAC TCA ACA GAT         685
Gln Glu Asp Phe Met Phe Ser Ser Asp Ala Gly Asp Asp Ser Thr Asp
                170                 175                 180

GGA TTC CAT GAC ATC TGT GGA CCA AAC AAG GAG CTG GAT GAA GAG ACC         733
Gly Phe His Asp Ile Cys Gly Pro Asn Lys Glu Leu Asp Glu Glu Thr
```

```
                  185                 190                 195
TGT CAG TGT GTC TGC AGA GCG GGG CTT CGG CCT GCC AGC TGT GGA CCC          781
Cys Gln Cys Val Cys Arg Ala Gly Leu Arg Pro Ala Ser Cys Gly Pro
            200                 205                 210

CAC AAA GAA CTA GAC AGA AAC TCA TGC CAG TGT GTC TGT AAA AAC AAA          829
His Lys Glu Leu Asp Arg Asn Ser Cys Gln Cys Val Cys Lys Asn Lys
        215                 220                 225

CTC TTC CCC AGC CAA TGT GGG GCC AAC CGA GAA TTT GAT GAA AAC ACA          877
Leu Phe Pro Ser Gln Cys Gly Ala Asn Arg Glu Phe Asp Glu Asn Thr
230                 235                 240                 245

TGC CAG TGT GTA TGT AAA AGA ACC TGC CCC AGA AAT CAA CCC CTA AAT          925
Cys Gln Cys Val Cys Lys Arg Thr Cys Pro Arg Asn Gln Pro Leu Asn
                250                 255                 260

CCT GGA AAA TGT GCC TGT GAA TGT ACA GAA AGT CCA CAG AAA TGC TTG          973
Pro Gly Lys Cys Ala Cys Glu Cys Thr Glu Ser Pro Gln Lys Cys Leu
            265                 270                 275

TTA AAA GGA AAG AAG TTC CAC CAC CAA ACA TGC AGC TGT TAC AGA CGG         1021
Leu Lys Gly Lys Lys Phe His His Gln Thr Cys Ser Cys Tyr Arg Arg
        280                 285                 290

CCA TGT ACG AAC CGC CAG AAG GCT TGT GAG CCA GGA TTT TCA TAT AGT         1069
Pro Cys Thr Asn Arg Gln Lys Ala Cys Glu Pro Gly Phe Ser Tyr Ser
295                 300                 305

GAA GAA GTG TGT CGT TGT GTC CCT TCA TAT TGG CAA AGA CCA CAA ATG         1117
Glu Glu Val Cys Arg Cys Val Pro Ser Tyr Trp Gln Arg Pro Gln Met
310                 315                 320                 325

AGC TAAGATTGTA CTGTTTTCCA GTTCATCGAT TTTCTATTAT GGAAAACTGT              1170
Ser

GTTGCCACAG TAGAACTGTC TGTGAACAGA GAGACCCTTG TGGGTCCATG CTAACAAGA        1230

CAAAAGTCTG TCTTTCCTGA ACCATGTGGA TAACTTTACA GAAATGGACT GGAGCTCATC       1290

TGCAAAGGC CTCTTGTAAA GACTGGTTTT CTGCCAATGA CCAAACAGCC AAGATTTTCC        1350

TCTTGTGATT TCTTTAAAAG AATGACTATA TAATTTATTT CCACTAAAAA TATTGTTTCT       1410

GCATTCATTT TTATAGCAAC AACAATTGGT AAAACTCACT GTGATCAATA TTTTTATATC       1470

ATGCAAAATA TGTTTAAAAT AAAATGAAAA TTGTATTTAT AAAAAAAAAA AAAAAA           1526

(2) INFORMATION FOR SEQ ID NO:4:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO:4:

Met Thr Val Leu Tyr Pro Glu Tyr Trp Lys Met Tyr Lys Cys Gln Leu
-24                 -20                 -15                 -10

Arg Lys Gly Gly Trp Gln His Asn Arg Glu Gln Ala Asn Leu Asn Ser
            -5                   1                   5

Arg Thr Glu Glu Thr Ile Lys Phe Ala Ala Ala His Tyr Asn Thr Glu
        10                  15                  20

Ile Leu Lys Ser Ile Asp Asn Glu Trp Arg Lys Thr Gln Cys Met Pro
25                  30                  35                  40

Arg Glu Val Cys Ile Asp Val Gly Lys Glu Phe Gly Val Ala Thr Asn
                45                  50                  55

Thr Phe Phe Lys Pro Pro Cys Val Ser Val Tyr Arg Cys Gly Gly Cys
            60                  65                  70
```

-continued

```
Cys Asn Ser Glu Gly Leu Gln Cys Met Asn Thr Ser Thr Ser Tyr Leu
             75                  80                  85
Ser Lys Thr Leu Phe Glu Ile Thr Val Pro Leu Ser Gln Gly Pro Lys
             90                  95                 100
Pro Val Thr Ile Ser Phe Ala Asn His Thr Ser Cys Arg Cys Met Ser
105                 110                 115                 120
Lys Leu Asp Val Tyr Arg Gln Val His Ser Ile Ile Arg Arg Ser Leu
                125                 130                 135
Pro Ala Thr Leu Pro Gln Cys Gln Ala Ala Asn Lys Thr Cys Pro Thr
            140                 145                 150
Asn Tyr Met Trp Asn Asn His Ile Cys Arg Cys Leu Ala Gln Glu Asp
            155                 160                 165
Phe Met Phe Ser Ser Asp Ala Gly Asp Asp Ser Thr Asp Gly Phe His
170                 175                 180
Asp Ile Cys Gly Pro Asn Lys Glu Leu Asp Glu Glu Thr Cys Gln Cys
185                 190                 195                 200
Val Cys Arg Ala Gly Leu Arg Pro Ala Ser Cys Gly Pro His Lys Glu
                205                 210                 215
Leu Asp Arg Asn Ser Cys Gln Cys Val Cys Lys Asn Lys Leu Phe Pro
            220                 225                 230
Ser Gln Cys Gly Ala Asn Arg Glu Phe Asp Glu Asn Thr Cys Gln Cys
            235                 240                 245
Val Cys Lys Arg Thr Cys Pro Arg Asn Gln Pro Leu Asn Pro Gly Lys
            250                 255                 260
Cys Ala Cys Glu Cys Thr Glu Ser Pro Gln Lys Cys Leu Leu Lys Gly
265                 270                 275                 280
Lys Lys Phe His His Gln Thr Cys Ser Cys Tyr Arg Arg Pro Cys Thr
                285                 290                 295
Asn Arg Gln Lys Ala Cys Glu Pro Gly Phe Ser Tyr Ser Glu Glu Val
            300                 305                 310
Cys Arg Cys Val Pro Ser Tyr Trp Gln Arg Pro Gln Met Ser
            315                 320                 325

(2) INFORMATION FOR SEQ ID NO:5:

(i) SEQUENCE CHARACTERISTICS:
        (A) LENGTH: 196 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:5:

Met Arg Thr Leu Ala Cys Leu Leu Leu Gly Cys Gly Tyr Leu Ala
1               5                  10                  15
His Val Leu Ala Glu Glu Ala Glu Ile Pro Arg Glu Val Ile Glu Arg
            20                  25                  30
Leu Ala Arg Ser Gln Ile His Ser Ile Arg Asp Leu Gln Arg Leu Leu
            35                  40                  45
Glu Ile Asp Ser Val Gly Ser Glu Asp Ser Leu Asp Thr Ser Leu Arg
 50                  55                  60
Ala His Gly Val His Ala Thr Lys His Val Pro Glu Lys Arg Pro Leu
 65                  70                  75                  80
Pro Ile Arg Arg Lys Arg Ser Ile Glu Glu Ala Val Pro Ala Val Cys
             85                  90                  95
```

```
Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
            130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195
```

(2) INFORMATION FOR SEQ ID NO:6:

(i) SEQUENCE CHARACTERISTICS:
        (A) LENGTH: 241 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:6:

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
            130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
            195                 200                 205

Thr Ile Arg Thr Val Arg Val Arg Arg Pro Pro Lys Gly Lys His Arg
            210                 215                 220

Lys Phe Lys His Thr His Asp Lys Thr Ala Leu Lys Glu Thr Leu Gly
225                 230                 235                 240
```

Ala (2) INFORMATION FOR SEQ ID NO:7:

(i) SEQUENCE CHARACTERISTICS:
        (A) LENGTH: 232 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:7:

```
Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
                180                 185                 190

His Leu Phe Val Gln Asp Pro Gln Thr Cys Lys Cys Ser Cys Lys Asn
                195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:8:

```
Pro Xaa Cys Val Xaa Xaa Xaa Arg Cys Xaa Gly Cys Cys Asn
 1               5                  10
```

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

ATGCTTCCGG CTCGTATG                                                    18

(2) INFORMATION FOR SEQ ID NO:10:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

GGGTTTTCCC AGTCACGAC                                                   19

(2) INFORMATION FOR SEQ ID NO:11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

CCACATGGTT CAGGAAAGAC A                                                21

(2) INFORMATION FOR SEQ ID NO:12:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

TGTAATACGA CTCACTATAG GGATCCCGCC ATGGAGGCCA CGGCTTATGC                  50

(2) INFORMATION FOR SEQ ID NO:13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

GATCTCTAGA TTAGCTCATT TGTGGTCT                                         28

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single -continued

```
        (D) TOPOLOGY: linear (ii) MOLECULE TYPE: cDNA (xi) SEQUENCE DESCRIPTION: SEQ ID NO:14:

CGCGGATCCA TGACTGTACT CTACCCA                                          27

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CGCTCTAGAT CAAGCGTAGT CTGGGACGTC GTATGGGTAC TCGAGGCTCA TTTGTGGTCT      60
```